United States Patent [19]
Chilton

[11] Patent Number: 6,107,334
[45] Date of Patent: Aug. 22, 2000

[54] DIETARY CONTROL OF ARACHIDONIC ACID METABOLISM

[75] Inventor: Floyd H. Chilton, Pilot Mountain, N.C.

[73] Assignee: Wake Forest University, Winston-Salem, N.C.

[21] Appl. No.: 09/028,256

[22] Filed: Feb. 23, 1998

[51] Int. Cl.$^7$ .......................... A61K 31/36; A61K 31/20; A61K 31/12

[52] U.S. Cl. ..................... 514/464; 514/558; 514/560; 514/679; 514/825; 514/826; 514/863

[58] Field of Search ..................................... 514/464, 558, 514/560, 679, 825, 826, 863

[56] References Cited

U.S. PATENT DOCUMENTS

| | | | |
|---|---|---|---|
| 4,309,415 | 1/1982 | Horrobin | 424/85 |
| 4,386,072 | 5/1983 | Horrobin et al. | 424/127 |
| 4,444,755 | 4/1984 | Horrobin | 424/145 |
| 4,560,514 | 12/1985 | Samuelsson et al. | 260/410 |
| 4,576,758 | 3/1986 | Morris | 260/405.5 |
| 4,666,701 | 5/1987 | Horrobin et al. | 424/10 |
| 4,888,326 | 12/1989 | Horrobin | 514/27 |
| 4,954,638 | 9/1990 | Young et al. | 548/546 |
| 4,965,075 | 10/1990 | Horrobin et al. | 424/638 |
| 5,141,958 | 8/1992 | Crozier-Willi et al. | 514/558 |
| 5,158,975 | 10/1992 | Guichardant et al. | 514/560 |
| 5,178,873 | 1/1993 | Horribin et al. | 424/422 |
| 5,328,691 | 7/1994 | Horrobin et al. | 424/401 |
| 5,336,496 | 8/1994 | Akimoto et al. | 424/195.1 |
| 5,352,700 | 10/1994 | Frithz et al. | 514/560 |
| 5,411,988 | 5/1995 | Bockow et al. | 514/560 |

FOREIGN PATENT DOCUMENTS

| | | |
|---|---|---|
| 0 598 365 A1 | 5/1994 | European Pat. Off. . |
| 0 598 365 B1 | 5/1994 | European Pat. Off. . |
| 0 711 503 A2 | 5/1996 | European Pat. Off. . |
| 0 713 653 A1 | 5/1996 | European Pat. Off. . |
| WO 96/31457 | 10/1996 | WIPO . |
| WO 97/21434 | 6/1997 | WIPO . |

OTHER PUBLICATIONS

Lowry, et al, Metabolic Support: Cyclic vs. Continuous Enteral Feeding With ω–3 and γ–Linolenic Fatty Acids: Effects on Modulation of Phospholipid Fatty Acids in Rat Lung and Liver Immune Cells, Journal of Parenteral and Enteral Nutrition, vol. 21, No. 3, Boston MA, May 1, 1996, pp. 123–132.

Dialog Search Patent Family printed Jun. 3, 1998.

Rothman et al., "Effects of unsaturated fatty acids on interleukin–1.beta. production by human monocytes," (abstract) Cytokine, 9(12):1008–12, 1997.

Byars et al., "Black currant seed oil as a source of polyunsaturated fatty acids in the treatment of inflammatory disease," (abstract) Biochem.Soc. Trans., 20(12), 139s, 1992.

International Search Report, PCT/US99/03120, Jun. 24, 1999.

*Primary Examiner*—Kimberly Jordan
*Attorney, Agent, or Firm*—Timothy S. Corder; Vinson & Elkins LLP

[57] ABSTRACT

The present invention is directed towards the control of inflammation. More specifically there are provided herein dietary fatty acid regimens that may be used to inhibit the increase of serum arachidonic acid when GLA is provided as a dietary supplement.

11 Claims, 10 Drawing Sheets

DIETARY CONTROL OF ARACHIDONIC ACID METABOLISM

BACKGROUND OF THE INVENTION

1. Field of the Invention

The present invention relates generally to the fields of lipid metabolism and dietary supplementation. More particularly, it concerns compositions and methods for inhibiting an increase in serum arachidonic acid of a mammal to which γ-linolenic acid (GLA) has been provided.

2. Description of Related Art

Arachidonic acid (AA) is a polyunsaturated fatty acid found in relatively small quantities in membranes of mammalian cells. Research over the last four decades has shown that the in vivo modulation of levels of arachidonic acid and oxygen-containing derivatives of arachidonic acid (known as eicosanoids) is intimately liked to human disease (for a review, see Samuelsson et al., 1987 and Chilton et al., 1997). For example, during inflammation, low levels of certain arachidonic acid derivatives render a protective response leading to enhanced disease resistance. However, these same molecules induce an autotoxic response leading to a variety of inflammatory disorders when produced in excessive quantities. Over the past three decades, the therapeutic utility of blocking the metabolism of arachidonic acid through multiple pathways including 5-lipoxygenase and cyclooxygenase I and II has become evident for the treatment of a wide range of inflammatory disorders.

Since arachidonic acid or its precursors found in cells and tissues must be derived from diets, it follows that diet may affect diseases controlled by arachidonic acid or its derivatives. This relationship was suggested in the 1960s by studies which showed differences in frequencies of inflammatory disorders among Greenland Eskimos and Danes (Chilton et al., 1996a; Dyerberg and Bang, 1979). Later studies showed similar differences between Japanese and Americans. These differences (Danes and Americans have much higher frequencies of inflammatory disorders including asthma, arthritis, psoriasis and acute myocardial infarction) were attributed, in large part, to the consumption by Danes and Americans, on Western diets, of high dietary quantities of precursor fatty acids of arachidonic acid (termed n-6 fatty acids) and arachidonic acid, offset by the low consumption of n-3 fatty acids.

Based on these observations, a number of dietary fatty acid reduction and supplementation strategies were undertaken in an attempt to influence arachidonic acid metabolism, eicosanoid production and clinical outcomes. These studies carried out over the last two decades have revealed that controlling dietary fatty acid intake in a number of animal models has great potential in reducing eicosanoid synthesis and ameliorating inflammation in models which mimic human arthritis, asthma or glomerulonephritis (Prickett et al., 1981; Kelley et al., 1985; Lefkowith et al., 1990; Rovin et al., 1990; Hurd et al. 1981).

These studies demonstrated that the formation of derivatives of AA and the subsequent effects of these compounds (eicosanoids) on cells and tissues are central processes in inflammation and allergy. Dietary fatty acid reduction and supplementation strategies have been utilized in animals and humans in an attempt to modulate cellular AA levels and metabolism and to ameliorate clinical inflammatory disorders. However, dietary modifications in humans on Western diets have shown only modest efficacy. If these observations are to prove useful in the treatment of such disorders, it is necessary to find more efficient dietary strategies to reduce eicosanoid generation in humans and to determine the mechanism(s) leading to this reduction.

In terms of inflammation, at least four dietary reduction and supplementation strategies have been utilized in both animals and humans in an attempt to influence eicosanoid production and clinical outcomes. One strategy has been to supplement "normal" diets with n-3 fatty acids. Here, there has been some controversy as to how effective these fatty acids are in reducing lipid mediators (eicosanoids) of inflammation (Chilton et al., 1993; Sperling et al., 1987; Strasser et al, 1984; Kojima et al., 1991; Galloway et al., 1985; Mori et al., 1987; Ahmed and Holub, 1984; Payan et al., 1986; Rosenthal, and Hills, 1986; Triggiani et al., 1990). For example, several studies report only modest inhibition of leukotrienes and PAF after n-3 fatty acid supplementation, while other investigations report more dramatic reductions (Chilton et al., 1993; Sperling et al., 1987; Strasser et al., 1984). The basis for these discrepancies is unclear at this time. In addition to eicosanoids, n-3 fatty acids have been shown to affect processes such as gene expression, cytokine generation and programmed cell death in a number of in vitro and in vivo settings (Endres et al., 1989; Clarke and Jump, 1996; Chandrasekar et al., 1995; Fernandes et al., 1994).

A second strategy to affect changes in AA metabolism in humans has been to remove dietary essential fatty acids from the diet. This eliminates sources of cellular AA that are derived from dietary linoleic acid (LA). Severe restrictions of LA intake in infants result in significant falls in levels of prostaglandin metabolites (Friedman et al., 1978). Wene and colleagues studied healthy men on fat-free eucaloric diets and found that LA levels in serum components fell dramatically within seven days of starting the diet (Wene et al., 1975). However, if calorie intake was then reduced (intermittent fasting), LA levels in serum increased. This LA repletion is probably due to mobilization of fatty acids from adipose tissue triglycerides.

A third strategy to reduce AA metabolism has been to restrict preformed AA in diets of humans. There are several conflicting studies in humans restricting preformed AA by the chronic avoidance of animal tissue with results varying from increases to moderate reductions in serum AA levels (Phinney et al., 1990; Sanders et al., 1978; Melchert et al., 1987). In contrast to studies restricting dietary AA, humans supplemented with AA (an additional 6 g/day) exhibit a pronounced increase in AA levels within plasma triglycerides, phospholipids, cholesterol esters, and platelet phospholipids (Seyberth et al., 1975). This increase within complex lipids is accompanied by an increase in eicosanoid generation and a marked decrease in the ADP threshold dose required to induce platelet aggregation.

A fourth strategy that has been utilized to influence AA metabolism is to supplement normal diets with oils (primrose and borage) rich in gamma linolenic acid (18:3, n-6). Such oils have been shown to improve clinical symptoms of patients with atopic dermatitis and rheumatoid arthritis (Leventhal et al., 1993; Miller et al., 1990; Horrobin, 1992; Zibok and Fletcher, 1992; Tate et al., 1989). The mechanisms by which GLA influences these inflammatory disorders has not been elucidated. In fact, it is paradoxical that providing a dietary precursor of AA, GLA, attenuates inflammation. It is known that a portion of GLA provided is elongated (by 2 carbons) in vivo to form dihomogammalinolenic acid (DGLA) (Horrobin, 1992; Zibok and Fletcher, 1992; Tate et al., 1989). DGLA can then be metabolized to oxygenated products, 15-OH-20:3. (15 HETrE) and prostaglandin $E_1$ by 15 lipoxygenase and cyclooxygenase, respectively (Miller et al., 1990; Horrobin, 1992). $PGE_1$ has been found to be anti-inflammatory in a variety of in vitro systems and animal models (Kerins et al., 1991). GLA supplementation also has been shown to reduce the capacity of some cells to produce AA-derived eicosanoids (Leventhal et al., 1993; Zibok and Fletcher, 1992).

Over the last six years, the inventor's laboratory has provided humans, on controlled diets, with a wide range of dietary fatty acid supplements and supplement combinations in an attempt to affect AA metabolism in humans (Chilton et al., 1993; Triggiani et al., 1990; Chilton-Lopez et al., 1996; Johnson et al., 1997). In these studies, the inventor has utilized well defined diets (prepared and fed in a General Clinical Research Center [GCRC]) and measurement techniques (negative ion chemical ionization GC/MS), which precisely determine fatty acid and eicosanoid levels in serum and inflammatory cells.

Although much work has been performed on the dietary supplementation of fats, many questions remain to be answered, including the determination of the capacity of different inflammatory cells to synthesize (elongate and desaturate) polyunsaturated fatty acids; the major mechanism(s) by which analogs (which can be induced by dietary supplementation) of AA influence eicosanoid generation and the development of dietary strategies that will produce natural antagonists of AA in inflammatory cells thereby reducing the synthesis of pro-inflammatory eicosanoids without increasing serum levels of AA. These and other questions are addressed by the present invention.

SUMMARY OF THE INVENTION

The present invention is directed to dietary strategies that will produce natural antagonists of AA in inflammatory cells, thereby reducing the synthesis of pro-inflammatory eicosanoids but without increasing serum levels of AA. The inventor has found that dietary supplements comprising GLA are beneficial in treating inflammatory disease through an increase in neutrophil GLA, but there is a concomitant increase in serum AA. The inventor has discovered that neutrophils, the inflammatory response cells, do not possess a $\Delta^5$ desaturase. Thus, the product of GLA elongation, DGLA can not be converted to AA and eicosanoids. However, in serum, DGLA formed from the elongation of GLA is converted to AA via the action of a $\Delta^5$ desaturase. This build-up of serum AA is likely to have harmful consequences in humans. For example, previous studies have demonstrated that increases in AA of this magnitude can increase platelet reactivity. Increases in sensitivity of platelets to stimuli in most cases are not desirable. The inventor has circumvented this problem by providing a $\Delta^5$ desaturase inhibitor, in this case, EPA in combination with the GLA, which prevents the serum increase in AA levels upon GLA administration.

Thus, in a preferred embodiment, the present invention provides a method of inhibiting increases in serum arachidonic acid of a mammal to which γ-linolenic acid (GLA) has been provided, comprising providing to the mammal a $\Delta^5$ desaturase inhibitor. In particular aspects, the mammal has an inflammatory disorder. In particularly preferred embodiments, the $\Delta^5$ desaturase inhibitor is eicosapentaenoic acid (EPA). Other $\Delta^5$ desaturase inhibitors contemplated to be useful in the present invention include sesamin, curcumin, heneicosapentaenoic acid and docosahexaenoic acid.

The GLA and EPA may be administered as free fatty acids or as fatty acyl esters. In particular aspects, the acyl esters are selected from the group consisting of triglycerides, ethyl esters, phospholipids, steryl esters and sphingolipids. The GLA and the EPA may be administered in a single pharmaceutical composition or as distinct pharmaceutical compositions or nutritional supplements.

Particular aspects of the present invention provide a method of treating an inflammatory disorder in a mammal comprising providing to the mammal a γ-linolenic acid in an amount effective to increase the amount of dihomo-γ-linolenic acid (DGLA) in inflammatory cells and the circulation of the mammal; and a $\Delta^5$ desaturase inhibitor in an amount effective to inhibit the formation of arachidonic acid in the serum of the mammal; wherein the increase in DGLA in the inflammatory cells of the mammal prevents the accumulation of arachidonic acid and decreases the inflammatory response in the mammal. The inflammatory diseases may include, for example, asthma, allergic rhinitis, allergic rhinoconjunctivitis arthritis, psoriasis, acute myocardial infarction glomerulonephritis, Crohn's disease, inflammatory bowel disease or any other disease that is mediated by lipid inflammatory mediators.

Also contemplated herein is a dietary supplement preparation comprising a GLA and EPA in an amount effective to increase the DGLA in the user such that the DGLA inhibits the formation of arachidonic acid in the inflammatory cells and the EPA inhibits the accumulation of arachidonic acid in the serum of the user. The dietary supplement may be further defined as comprising from about 1 g to about 15 g of GLA per daily dose. In other embodiments, the dietary supplement is defined as comprising from about 1 g to about 10 g of EPA per daily dose.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 17A. GLA supplementation in combination with EPA. FIG. 17B. Stearidonic Acid Supplementation

ABBREVIATIONS

AA, 20:4, arachidonic acid; EPA, 20:5 (n-3), eicosapentaenoic acid; LA, 18:2, linoleic acid; EFA, essential fatty acid; PUFA, polyunsaturated fatty acid; GLA, 18:3 (n-6), gammalinolenic acid; DGLA, 20:3 (n-6), dihomogammalinolenic acid; SDA, 18:4 (n-3), stearidonic acid; ω-3 AA, 20:4 (n-3), PC, phosphatidylcholine; PE, phosphatidylethanolamine, PL phosphatidylinositol; GPC, sn-glycero-3-phosphocholine; GCRC, General Clinical Research Center; GC/MS, gas chromatography/mass spectrometry; NICI negative ion chemical ionization; TNF, tumor necrosis factor; FMLP, n-formyl-methionine-leucinephenylalanine; TLC, thin layer chromatography; HPLC, high pressure liquid chromatography; LTB$_4$, leukotriene B$_4$; LTB$_5$, leukotriene B$_5$; LTC$_4$, leukotriene C$_4$; PAF, platelet activating factor, HBSS, Hank's Balanced Salt Solution; BALF, bronchoalveolar lavage fluid; EAR, early asthmatic response; LAR, late asthmatic response.

DESCRIPTION OF ILLUSTRATIVE EMBODIMENTS

The present invention provides a dietary strategy, comprising a combination of GLA with eicosapentaenoic acid (EPA). This combination can be utilized in humans to synthesize close structural analogs (antagonists) of AA in the neutrophils without concomitant increases in serum arachidonate. Thus, the antagonist of AA metabolism in the neutrophils and other inflammatory cells prevents the synthesis of the eicosanoids responsible for an inflammatory response.

Figure 17A:
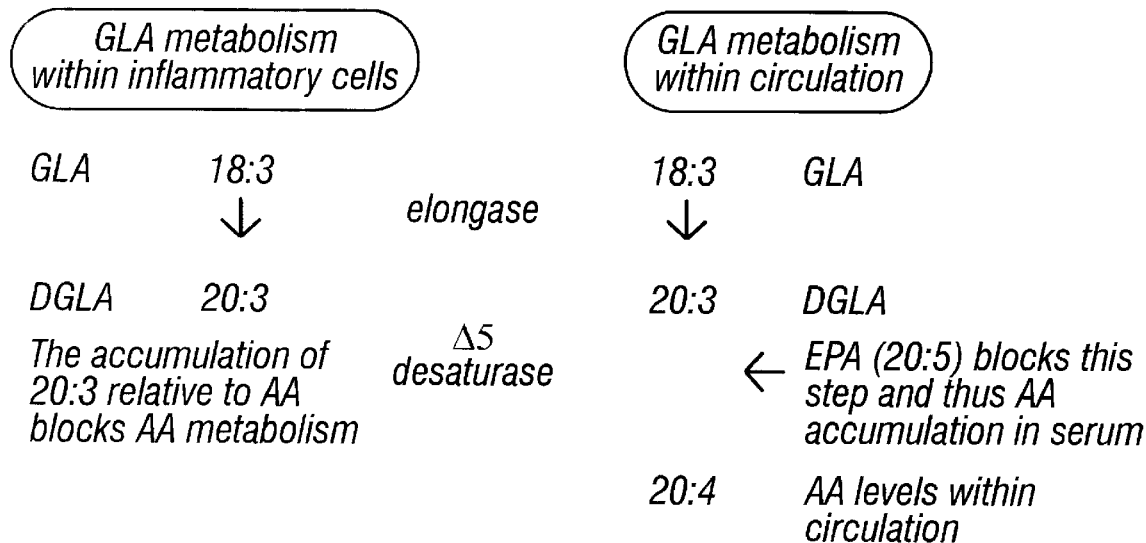
FIG. 17A and FIG. 17B. The two in vivo approaches to be used in order to synthesize close structural analogues of AA without affecting circulating AA levels.

GLA administration to humans can effectively block AA metabolism, block the synthesis of AA products and mitigate the clinical symptoms of inflammatory disorders. When GLA is administered as a dietary supplement, an endogenous elongase activity in inflammatory cells synthesizes a close analogue of AA, DGLA (FIG. 17A). The inventor has discovered that certain inflammatory cells cannot further desaturate DGLA to AA because they lack a $\Delta^5$ desaturase. However, in human circulation, GLA becomes elongated to DGLA, and then further desaturated to AA. This leads to a marked increase in AA level in the circulation as a result of GLA administration. The increased AA in the circulation has been shown to have potentially detrimental effects such as platelet reactivity in humans (Seyberth et al., 1975).

The present invention is a method of providing high concentrations of GLA to humans without causing a concomitant accumulation of serum AA in the circulation. Thus, high concentrations of GLA can be administered to humans to synthesize DGLA in inflammatory cells thereby inhibiting AA metabolism, eicosanoid synthesis and attenuating the signs and symptoms of inflammatory disorders without the significant side effect of circulatory AA accumulation. Specifically in the present invention, GLA is administered to humans in combination with $\Delta^5$ desaturase inhibitors including EPA. The present inventor has shown that this combination of GLA and the $\Delta^5$ desaturase inhibitor, EPA, causes a marked accumulation of DGLA in the circulation and in inflammatory cell lipids without causing an increase in accumulation of AA in serum lipids. Thus, the present invention provides combined compositions of EPA and GLA for the treatment of inflammatory disorders such as psoriasis, rheumatoid arthritis, inflammatory bowel disease, Crohn's disease, ulcerative colitis, asthma or any other disease, syndrome or disorder that is mediated by lipid inflammatory mediators.

The present invention provides methods and compositions for altering the serum arachidonic acid of a mammal by providing a $\Delta^5$ desaturase inhibitor in an amount effective to increase the amount of GLA in the circulation of the mammal without the accumulation of AA in the serum of said mammal. In preferred aspects, the present inventor has found that EPA is an inhibitor of $\Delta^5$ desaturase activity in the serum, of mammals. Thus, administration of a combination of GLA and EPA will serve to prevent the synthesis of AA and its metabolites in neutrophils, whilst inhibiting the accumulation of AA in the serum. These methods and compositions are discussed in further detail herein below.

Sources of Fatty Acids for Use in Dietary Supplements

The fatty acyl compositions of the present invention may be obtained from a variety of sources. These acids may form part of a phospholipid, steryl ester, a sphingolipid, a glyceride, such as a di- or triglyceride or may be present as free fatty acids. For a comprehensive treatise of the synthesis and fatty acyl containing lipids, one of skill in the art is referred to "Lipid: Chemistry, Biochemistry and Nutrition" (Mead et al., 1986. Plenum Press, New York, incorporated herein by reference). More particularly, the distribution of fatty acids in tissue lipids is described in Chapter 5. Of particular relevance are chapters 11, 14, 15, 17, and 18 which describe synthesis and metabolic relevance of eicosanoids, triacylglycerols, steryl esters, phosphoglycerides and sphingolipids.

GLA may be obtained from sources such as oils of evening primrose, borage, blackcurrant, and various fungi and algae including Mucor, Rhizoptis and Spirulina. DGLA may be synthesized from GLA or alternatively, may be obtained from a variety of animal tissues including, liver, kidneys, adrenals or gonads. AA can also be isolated from similar tissues, or from egg yolk, and can also be found in various fungal and algal oils. EPA may be found in marine oils and various algal and fungal oils. Of course, although rather difficult and expensive, all the fatty acids may also be chemically synthesized de novo.

The present invention is described in terms of methods and pharmaceutical compositions, but it is understood that the GLA, EPA and any other fatty acid of the present invention may be incorporated into a dietary margarine or other foodstuff. Pharmaceutical and dietary compositions comprising fatty acyl components are well known to those of skill in the art and have been described in U.S. Pat. Nos. 4,666,701; 4,576,758; 5,352,700; 5,328,691; 4,444,755; 4,386,072; 4,309,415; 4,888,326; 4,965,075 and 5,178,873; and in EP 0 713 653; EP 0 711 503; WO 96/31457 and WO 97/21434 (each of which is specifically incorporated herein by reference).

$\Delta^5$ desaturase Inhibitors

As discussed earlier, AA and compounds derived therefrom are central mediators of inflammatory and allergic responses. One mechanism for ameliorating the deleterious effects of these compounds is through dietary control. One such manipulation involves the production or use of natural antagonists of AA at the sites of action of these compounds inflammatory cells. Dietary supplementation with GLA has been shown to be effective at lowering inflammatory response. It appears that although neutrophils (inflammatory response cells) take up GLA and elongate it to DGLA, there is no subsequent production of the eicosanoids that mediate inflammatory response. This is because neutrophils do not possess a $\Delta^5$ desaturase, thus the DGLA produced is not desaturated to AA. However, there is a problem with indiscriminate provision of GLA in that although neutrophils lack a $\Delta^5$ desaturase, other cells in the circulatory system do have $\Delta^5$ desaturation capabilities and such cells readily elongate GLA to DGLA and desaturate the DGLA to AA. This increased circulatory AA is a potently harmful agent. The present inventor has found that this harmful accumulation of AA in the circulation of GLA-supplemented individuals can be prevented by a concomitant provision of a $\Delta^5$ desaturase inhibitor.

EPA is an $\omega$-3, 20 carbon fatty acid that contains five double bonds (20:5), and as such is a structural analogue of AA (20:4). EPA has been shown to act as a $\Delta^5$ desaturase inhibitor, presumably via a feedback inhibition mechanism. Methods of producing this fatty acid have been well described in the art (e.g. U.S. Pat. Nos. 5,683,898; 5,567,732; 5,401,646; 5,246,842; 5,246,841; 5,215,630 each incorporated herein by reference). The present invention, in preferred embodiments, employs EPA as a $\Delta^5$ desaturase inhibitor to be administered in a nutritional supplement to those individuals receiving GLA-supplements, in order to prevent the accumulation of AA in the circulation of said individuals.

In certain embodiments, it is contemplated that other inhibitors of $\Delta^5$ desaturase will also be useful, such compounds include members of the sesamin family, members of the curcumin family and other fatty acids such as docosahexaenoic acid, and heneicosapentaenoic acid. U.S. Pat. No. 5,674,853, which is specifically incorporated herein by reference, describes the use of lignins from the sesamin family in combination with saponins compositions as enteral formulations for treatment of infection and inflammation. Such sesamins will be useful in the context of $\Delta^5$ desaturase inhibition described herein.

U.S. Pat. No. 5,336,496, incorporated herein by reference, describes other inhibitors of $\Delta^5$ desaturase that will be useful in the context of the present invention. In general terms, the $\Delta^5$ desaturase inhibitors described therein include lignan compounds, curcumin and piperonyl butoxide. As used herein the term "lignan" includes compounds such as sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, and 2-(3,4-methylenedioxyphenyl)-6-(3-methoxy-4-hydroxyphenoxy)-3,7-dioxabicyclo[3.3.0]-octane.

Methods of producing and separating these compounds are well known to those of skill in the art. For example U.S. Pat. No. 5,209,826 describes a method of separating sesamin and episesamin. It is contemplated that the present invention may use such methods in obtaining $\Delta^5$ desaturase inhibitors as such U.S. Pat. No. 5,209,826 is incorporated herein by reference. In other embodiments, the present invention employs microorganisms for producing fatty acids as inhibitors of $\Delta^5$ desaturase, such techniques are well known to those of skill in the art (e.g., Shimizu et al., 1988; Shimizu et al., 1989).

Methods for the synthesis of curcumin-related compounds have been described in U.S. Pat. No. 5,679,864 (incorporated herein by reference). This involves reacting the enol form of a 2,4-diketone with a monocarbocyclic aldehyde in the presence of an organic amine catalyst. The reactants are dissolved in a highly polar, aprotic organic solvent. The curcumin-related product is recovered in crystalline form by precipitation from the reaction mass and solvent recrystallization and may be further purified using chromatographic techniques. The synthesis of naturally occurring curcuminoids and related compounds is well known in the art, the skilled artisan is referred to e.g., Pedersen, et al., 1985; Arrieta et al., 1991 and Roughly et al., 1973, for guidance regarding detailed description of such synthesis and characterization.

Methods of Detection and Purification

The present invention concerns the provision, for example, as dietary supplements of a number of fatty acyl compositions. The fatty acid metabolism in circulatory and neutrophil cells has a balance of different precursors and substrates of arachidonic acid metabolism. In providing exogenous fatty acids as dietary supplementation, this baseline balance of fatty acids likely will be altered. In certain instances it may be necessary to monitor the levels of the different fatty acids present in an individuals circulation and/or neutrophils. The present invention encompasses methods for the determination of the fatty acyl content of cells. These methods can also be employed for purifying fatty acids for inclusion as part of a dietary supplement. Generally, these methods will follow the methods described in the examples of the initial characterization of lipid content.

Chromatographic Methods of Detection

Briefly, one generally will isolate the lipid components of a cell as described herein. Separation of lipid components from (i) non-lipid components and (ii) each other will then permit quantitation of the different lipid species. Quantitation of separated components may be achieved by any standard methodology, that would include photodensitometric scanning of TLC plates or scintillation counting of membrane bound or liquid samples separated by various chromatographic techniques.

Any of a wide variety of chromatographic procedures may be employed. For example, thin layer chromatography, gas chromatography, high performance liquid chromatography, paper chromatography, affinity chromatography or supercritical flow chromatography may be employed. See Freifelder, 1982.

Partition chromatography is based on the theory that, if two phases are in contact with one another, and if one or both phases constitute a solute, the solute will distribute itself between the two phases. Usually, partition chromatography employs a column which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatography are paper chromatography and thin-layer chromatography (TLC); together these are called adsorption chromatography. In both cases, the matrix contains a bound liquid. Other examples of partition chromatography as gas-liquid and gel chromatography.

Paper chromatography is a variant of partition chromatography that is performed on cellulose columns in the form of a paper sheet. This technique may be useful in identifying and characterizing the lipid content of a particular sample. Cellulose contains a large amount of bound water even when extensively dried. Partitioning occurs between the bound water and the developing solvent. Frequently, the solvent used is water. Usually, very small volumes of the solution mixture to be separated are placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

High Performance Liquid Chromatography (HPLC) is characterized by a very rapid separation with extraordinary resolution of peaks. This is achieved by the use of very fine particles and high pressure to maintain an adequate now rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

Monoclonal Antibody Production and Methods of Detection Using Antibodies

Another method of detecting the lipids of the present invention may employ antibodies. In these embodiments, antibodies against enzymes that participate in lipid metabolism will be useful in the present invention, primarily in assays for the detection of such lipids. Means for preparing and characterizing antibodies are well known in the art (see, e.g., Antibodies: A Laboratory Manual, Cold Spring Harbor Laboratory, 1988; incorporated herein by reference).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster, a sheep or a guinea pig. Because of the ease of use and relatively large blood volume of rabbits, a rabbit is a preferred choice for production of polyclonal antibodies.

A monoclonal antibody can be readily prepared through use of well-known techniques such as those exemplified in U.S. Pat. No 4,196,265, herein incorporated by reference.

Typically, a technique involves first immunizing a suitable animal with a selected antigen in a manner sufficient to provide an immune response. After a sufficient time to induce an immune response, spleen cells from the immunized animal are then fused with cells of an immortal myeloma cell. A number of immortal myeloma cells are available and the choice of the immortal cell is within the skill of an artisan. Immortal myeloma cells lack the salvage pathway of synthesizing nucleotides.

The fused spleen/myeloma cells are cultured in a selective medium to select fused spleen/myeloma cells from the parental cells. Fused cells are separated from the mixture of non-fused parental cells by the addition of agents that block the de novo synthesis of nucleotides in the tissue culture media. Unfused myeloma cells lack the enzymes necessary to synthesize nucleotides from the salvage pathway and are selectively killed in the selective media. Unfused lymphocytes also do not continue to grow in tissue culture. Thus, only cells that have successfully fused (hybridoma cells) can grow in the selection media. The hybridoma cell produces a monoclonal antibody.

Certain aspects of the present invention relates to the detection of fatty acylated lipids. One such detection method uses immunoassays for fatty acids. Antibodies and other toxin binding proteins (i.e., cell surface receptors) that recognize a product or by-product of fatty acyl biosynthesis are contemplated to be useful in the detection of fatty acids in the immunoassays.

Immunoassays encompassed by the present invention include, but are not limited to those described in U.S. Pat.

No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful.

In one exemplary ELISA, the antibodies are immobilized onto a selected surface exhibiting protein affinity, such as a well in a polystyrene microtiter plate. Then, a test composition suspected of containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is a simple "sandwich ELISA". Detection may also be achieved by the addition of a second antibody specific for the desired antigen followed by the addition of a third antibody that has binding affinity for the second antibody, with the third antibody being linked to a detectable label.

In another exemplary ELISA, the samples suspected of containing the desired antigen are immobilized onto the well surface and then contacted with the antibodies of the invention. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies may also be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for 2 hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g. using a visible spectra spectrophotometer. Alternatively, the label may be a chemiluminescent one. The use of such labels is described in U.S. Pat. Nos. 5,310,687, 5,238,808 and 5,221,605.

Pharmaceutical Compositions and Routes of Administration

The nutritional compositions of the present invention will have an effective amount of a $\Delta^5$ desaturase inhibitor and GLA, alone or in combination with other dietary supplements. Such compositions will generally be dissolved or dispersed in a pharmaceutically acceptable carrier or medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other fatty acid supplements, can also be incorporated into the compositions.

The compounds are generally formulated for oral administration, such pharmaceutically acceptable forms include, e.g., tablets or other solids for oral administration; time release capsules and lozenges; and any other form currently used, including cremes, and liquids, for example syrups, suspensions or emulsions, inhalants and the like.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavoring or coloring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Preferably the composition is in unit dose form such as a tablet or capsule. Each dosage unit for oral administration contains preferably from about 1 to about 15 mg of GLA and about 1 to about 10 g of EPA or a pharmaceutically acceptable salt thereof calculated as the free base.

The pharmaceutically acceptable compounds of the invention will normally be administered to a subject in a daily dosage regimen. For an adult patient this may be, for example, an oral dose of GLA between 1 g and 15 g and an oral dose of EPA between 1 g and 10 g. The pharmaceutical compositions are administered 1 to 4 times per day. Thus in particular embodiments, the present invention contemplates a composition comprising a 1:1 (w/w) ratio of GLA:EPA, wherein there may be 1, 2, 3, 4, 5, 6, 7, 8, 9, or 10 grams of GLA. In other embodiments there may be a 2:1 ratio of (w/w) ratio of GLA:EPA, wherein there may be 1, 2, 3, 4, 5, 6, 7, 8, 9, 10, 11, 12, 13 14 or 15 grams of GLA. Of course, the ratio of GLA:EPA administered may be varied from that disclosed herein above, any amount of EPA including 1, 2, 3, 4, 5, 6, 7, 8, 9 or 10 grams of EPA may be administered with any amount of GLA including 1, 2, 3, 4, 5, 6, 7, 8, 9, 10, 11, 12, 13, 14 or 15 grams of GLA. Such amounts of either supplement may be admixed in one composition or may be in distinct compositions.

The preparation of a composition that contains the $\Delta^5$ desaturase inhibitor (EPA) and GLA compounds alone or in combination with other supplements as active ingredients will be known to those of skill in the art in light of the present disclosure. Typically, such compositions can be prepared as liquids for capsules; solid forms or suspensions; the preparations can also be emulsified.

The dietary supplement comprising the combined $\Delta^5$ desaturase inhibitor and GLA formulations of the present invention may be in the form of ingestible liquids. For example European patent application number EP 0713 653 A1 and EP 0711 503 A2 (incorporated herein by reference) describe fruit juices and milk based liquids that can be fortified with GLA and other dietary supplements. In alternative embodiments, the combined $\Delta^5$ desaturase inhibitor and GLA formulations of the present invention may be incorporated into a dietary margarine or other foodstuff.

Solutions of the active compounds as free base or pharmacologically acceptable salts can be prepared in liquid suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical formulations suitable for ingestion include sesame oil. evening primrose oil, peanut oil or aqueous propylene glycol; and sterile powders. In all cases it is desirable to keep the formulation sterile and stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the compositions can be brought about by the use in the compositions of agents delaying absorption, for example, aluminum monostearate and gelatin.

Sterile compositions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders, the preferred methods of preparation are vacuum-drying and freeze-drying techniques which yield a powder of the active ingredient.

Upon formulation, the active ingredients will be administered in a manner compatible with the dosage formulation and in such amount as is therapeutically effective. The formulations are easily administered in a variety of dosage forms, such as tablets containing measured amounts of active ingredient, with even drug release capsules and the like being employable. The amounts of active ingredients in the formulations of the present invention will be similar to fatty acid supplements currently available, those of skill in the art are referred to the Physicians Desk Reference for more comprehensive details on currently used dosages of food supplements. Some variation in dosage will necessarily occur depending on the condition of the subject being treated. The person responsible for administration will, in any event, determine the appropriate dose for the individual subject.

Kits

All the essential materials and reagents required for determining fatty acyl levels in a sample may be assembled together in a kit. When the components of the kit are provided in one or more liquid solutions, the liquid solution preferably is an aqueous solution, with a sterile aqueous solution being particularly preferred.

For the detection of lipid components, the kit may contain materials for chromatographic separation, such as columns, beads, resins, gel matrices, filters, TLC plate, buffers and appropriate solvents. Alternatively, if the detection is via immunologic means, the kit may contain antibodies directed to the lipids, secondary antibodies that binding primary antibodies, labels or signal generating compounds (either conjugated or unconjugated) and various reagents for the generation and detection of signals.

For in vivo use, an inhibitor of $\Delta^5$ desaturase, alone or in combination with other dietary supplements may be formulated into a single or separate pharmaceutically acceptable syringeable composition. In this case, the container means may itself be an inhalant, syringe, pipette, dropper, or other such like apparatus, from which the formulation may be applied to the body, injected into an animal, or even applied to and mixed with the other components of the kit.

The components of these kits may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the $\Delta^5$ desaturase inhibitor and GLA and/or other supplements, or explaining the assays for determining lipid levels in samples.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell and serum preparations

Neutrophils. Neutrophils are obtained from venous blood of healthy human donors as described (Lykens et al., 1992).

Eosinophils. Eosinophils are purified by negative immunomagnetic selection using monoclonals against FcKRIII (CD 16) present on neutrophils. Antibody tagged neutrophils is then incubated with anti-mouse IgG conjugated magnetic beads and removed by filtration over a magnetized steel wool column.

Monocytes. A mononuclear cell layer is obtained from normal human blood after centrifugation over isolymph and washing in HBSS without $Ca^{2+}$ or $Mg^{2+}$, with 0.1% gelatin and 2 mM glucose, pH 7.4. Mononuclear cells are further separated by centrifugation over discontinuous Percoll gradients (45°/50.5%, 15 min, 300× g) to obtain a rough separation of monocytes from lymphocytes, washing, and then centrifuged over 48% Percoll (15 min, 300× g) to remove contaminating lymphocytes.

Alveolar Macrophage (AM). BAL fluid samples are strained through a monolayer of coarse mesh surgical gauze and total cell counts and differentials determined. Cells are pelleted, resuspended in PBS, and washed 3 times. In normal individuals, ~1 to $1.5 \times 10^7$ total cells are expected with 85% of harvested cells being AM. When necessary (to attain a population of at least 85% AM), AM are further purified by centrifugation (300× g, 15 min) over 48% Percoll. Cells are washed (3×) in buffer and resuspended at $1 \times 10^7$ cells/ml in HBSS.

Serum isolation. Serum is extracted from 2 ml of venous blood from donors. Briefly, blood samples are incubated at 37° C. for 30 min. Blood clots are removed from the serum by centrifugation (600× g, 10 min). Residual red blood cells are removed from the serum by centrifugation using a Beckman Microfuge E for 5 min. After the addition of 1.9 ml of water to a 0.1 ml aliquot of the serum lipids are extracted by the method of Bligh and Dyer (Bligh and Dyer, 1959; Chilton et al., 1983). A portion (5%) of the extracted lipids are used to determine the mole quantities of fatty acids by GC/MS. Serum components are isolated into individual glycerolipid classes by TLC (System II or normal phase HPLC (Bligh and Dyer, 1959).

Chromatography Techniques

HPLC of phospholipid classes. Phospholipid classes (PE, PS, PL, and PC) are separated by normal phase HPLC using an Ultrasphere-Si column (4.6×250 mm) eluted initially with hexane:2-propanol:ethanol:25 mM phosphate buffer (pH 7.4):acetic acid (490:367:100:30:0.6, v/v) at a flow rate of 1 ml/min. After 5 min, the composition of the phosphate buffer is increased to 5% over a 10 min period to elute all phospholipids.

TLC of phospholipid subclasses. Phospholipid subclasses (diacyl-, alkylacyl-, alk-1-enylacyl-) are separated as diglyceride acetates or benzoates on silica gel G plates developed in benzene/hexane/ ether (50:45:4. v/v). Briefly, the phosphobase moiety of phospholipids is removed by phospholipase C hydrolysis followed by the addition of acetic anhydride/pyridine (5:1, v/v).

HPLC Of leukotrienes. Leukotrienes are separated by reverse phase HPLC utilizing an Ultrasphere ODS column (2.1 mm×250 mm: Rainin Instrument Co, Woburn, Mass.) eluted with methanol/water/phosphoric acid (550:450:0.2 v/v, pH 5.7) as the mobile phase at 0.3 ml/min. After 5 min the methanol composition of the mobile phase is increased from 55% to 100% over a 20 min period. The mole quantities of each leukotriene are determined by examining its UV optical density at 270 nm. Individual peaks are integrated and their recoveries normalized by comparing these integrated areas to that of $PGB_2$ added as an internal standard.

GC/MS analysis of fatty acids and lipid mediators

Base hydrolysis and fatty acid analysis by GC/MS. Free fatty acids are obtained from glycerolipids by base hydrolysis using 2 N KOH (30 min, 60° C.). After the addition of an equal volume of water, the pH of the reaction mixture is adjusted to 3 using 6 N HCl. Free fatty acids are then extracted with ethyl ether and converted to pentafluorobenzylesters using an equal volume of 20% pentafluorobenzylchloride in acetonitrile and 20% diisopropylethylamine in acetonitrile. The carboxylate anion of all fatty acids of interest and $[^2H_3]$-stearic acid and $[^2H_8]$-arachidonate (internal standard) are analyzed by NICI GC/MS using a Hewlett Packard mass spectrometer (HP 5989A).

Analysis of eicosanoids by GC/MS. Eicosanoids from ethyl acetate extracts of supernatant fluids are converted to methoxime-pentafluorobenzyl ester trimethylsilyl derivatives. These derivatives of $LTB_4$, $LTB_5$, $^2H_4$-$LTB_4$, $PGE_2$, $PGE_1$, $^2H_4$ $PGE_2$ and $^2H_4$ $PGE_1$ (internal standard) are analyzed on an HP selective mass detection system (Hewlett Packard 5989A) by selected ion monitoring techniques to record carboxylate anions at m/z 479, 477, 483, 524, 526, 528 and 530, respectively.

Urinary LTE4

Aliquots of urine are spiked with $^3H$-$LTE_4$ and stored at −70° C. Urinary $LTE_4$ is then measured using the methods of Manning et al. (1990) utilizing reverse phase HPLC followed by RIA (Christie, 1985). Recovery is determined using the added $[^3H]$-$LTE_4$ as an internal standard. LTE4 levels are expressed relative to urinary creatinine.

Subjects and controlled diets.

Subject. Subjects are recruited by poster advertisements from the Medical Center staff and students. Inclusion criteria require healthy, normal men and women of all races, 21 to 55 years old; subjects who consume an omnivorous, nutritionally adequate diet consisting of at least 25% of calories from fat. Volunteers who are within 10% of ideal body weight (IBW) and do not exceed 30% and 35% body fat for men and women, respectively (as determined by anthrometric measurements in the GCRC). Diet compositions are determined by the food frequency questionnaire component of the Health Habits and history Questionnaire developed by the NCI (Shin et al., 1994; Wenzel et al., 1997).

Exclusion criteria include persons with any chronic or acute disease as determined by self report or physical screening; who are vegetarians or vegans; who are lactose or egg intolerant; who use drugs which affect AA release and subsequent metabolism (steroidal and non-steroidal anti-inflammatories); with serum cholesterol levels above 220 mg/cd; who are unable or unwilling to strictly adhere to a precise, restricted diet; who are unwilling to be randomly assigned to the diet group for whatever protocol the subject volunteers; who are smokers.

Diet. Composition of the diets are based on the USDA Handbook 8 and The Nutrition Data System from The Nutritional Coordinating Center of the University of Minnesota. For each of the protocols outlined above, the menus are designed with adjustments for each subjects energy needs. Basal energy expenditure is determined by the Harris-Benedict Equations:

Basal energy expenditure (BEE) for men=65+(13.7×Wt(kg))+(5×Ht(cm))−(6.8×age(yr))

[for women=655+(9.6×Wt(kg))+(1.8×Ht(cm))−(4.7×age(yr))]

Total daily energy needs equal the BEE times an activity factor of from 1.3 for ambulatory but sedentary to 1.5 for the more active persons. Body weight is monitored each day when the subjects come to the Center to receive their meals. Calorie levels are adjusted appropriately.

Procedures and Specimens Collection used in Human Model of Atopic Asthma

Clinical data on each patient is entered into a database consisting of the following elements. Demographic data (age, sex, race, smoking history), and the data elements used to fulfill the above diagnostic criteria, spirometric data, presence of atopy (positive "prick" skin testing to respirable antigens), presence of LAR to inhaled antigen, and presence of allergic rhinoconjunctivitis.

Allergen skin testing—Atopic asiatic subjects are identified by skin testing using the skin prick method at a 1:10 (wt/vol) dilution of 20 stock antigen solutions (Greer Laboratories. Lenoir, N.C.). Subjects must not be receiving immunotherapy, nor may they be treated with systemic corticosteroids for a minimum of 4 wk. Short acting antihistamines are avoided for at least 24 h and long acting for at least 7 days. Atopic subjects are defined as those with a positive response consisting of a wheal of at least 3 by 3 mm. to one or more antigens, with an appropriately negative saline control.

Allergen Inhalation Challenge—The immediate (early) asthmatic response (EAR) or late asthmatic response (LAR) is studied under controlled conditions using inhaled antigenic challenge. The inventor intends to do this in volunteer patients with asthma using a previously described protocol (Smith et al., 1993). Atopic asthmatics will undergo inhaled allergen challenge followed by BAL according to the following protocol. Subjects must have no lung disease other than asthma, and, on the day of testing, must have a baseline $FEV_1>70\%$ of predicted. Subjects must not be receiving immunotherapy, nor may they be treated with cromolyn sodium or corticosteroids (inhaled or systemic) or leukotrienie antagonist for a minimum of 4 wk. Short-acting antihistamines are avoided for at least 24 h and intermediate acting for 7 days (astemizole for 6 weeks). Theophylline preparations are withheld for 24 h prior to challenge and beta-agonists for 8 h prior to challenge. On the day of challenge, subjects must be wheeze-free, with an $FEV_1>$than 80% of the previously observed highest value. If the patient has an intercurrent respiratory infection, inhalation challenge is postponed for at least 6 wk. Antigens to which the subject is perennially exposed (e.g., mite, cat) are utilized whenever possible to minimize the impact of seasonal variations in environmental exposure to the specific antigen. Further, antigen testing is conducted out of the respective allergen season, or after attempts to minimize environmental exposure (e.g., to mites or cats) have been implemented. Antigenic challenge generally begins between 7:30 and 8:00 am and the patient is monitored for a minimum of 12 h following antigenic challenge. Subjects inhale allergen to which they have previously demonstrated skin sensitivity beginning at 1:1.000.000 dilution (wt/vol) and proceeding with logarithmically increasing concentrations to 1:100. The subject breathes quietly from a continuous hand-held nebulizer for 2 min at each concentration. Following each concentration, the $FEV_1$ is measured at 5 min intervals (DS Plus, Warren E. Collins, Inc., Braintree, Mass.). If the $FEV_1$ does not fall by 20% after 15 min, the next higher concentration is administered. Once a 20% drop in $FEV_1$ is measured, or following the highest concentration, spirometry is performed every 15 min for the first hour and then hourly for the next 11 h. Patients experiencing symptomatic bronchospasm following initial antigenic inhalation may receive a short acting inhaled beta-agonist bronchodilator agent (isoproterenol). This has no effect on the subsequent late asthmatic response (LAR). An LAR is defined as a 15% or greater fall in $FEV_1$ from the prechallenge baseline value occurring between 3 to 12 h after challenge.

Bronchoalveolar lavage Subjects whose $FEV_1$ immediately preceding bronchoscopy is less than 60% of prechallenge baseline do not undergo BAL to minimize further acute diminution of lung function and to maximize subject safety. Fiberoptic bronchoscopy is performed following methodologies previously detailed in the literature (Wenzel et al., 1991; Zehr et al., 1989). Briefly, the fiberoptic bronchoscope is introduced into the lower airways transnasally following nebulized 4% Xylocaine. topical anesthesia and benzodiazepine sedation, titrated to patient comfort Isoproterenol, 1 puff. 130 μg is administered 10 min before bronchoscopy. Bronchoalveolar lavage (BAL) is obtained from the right middle lobe or lingula utilizing six 50 ml aliquots (200 ml total volume) of sterile normal saline without preservatives, warmed to 37° C. The amount of BAL returned is recorded and the specimen promptly processed. The right middle lobe or lingula is routinely used to maximize the uniformity of specimen yield as the return from BAL is dependent upon many factors but especially airway geometry and gravity. These areas tend to drain spontaneously by gravity in supine patients. This improves the return of fluid from the lavage as well as minimizing the amount of retained fluid within the lung in these patients.

BAL samples are strained through a monolayer of coarse-mesh surgical gauze and total cell yield determined by taking a small aliquot of the pooled, well mixed fluid, and counting the cells in a Neubauer hemocytometer. BAL cell count is expressed as the total number of cells recovered by lavage and as the number of cells per ml of recovered BAL fluid. A small aliquot is then cytocentrifuged (Shandon Southern Cytospin) for 5 min at 4,500 RPM, air dried, and stained by a modified Wright-Giemsa stain. A 300 cell differential count is performed where alveolar macrophages and other leukocytes are enumerated. The number of ciliated or squamous epithelial cells present are noted, but are not included in the differential count. Quantification of the cellular populations recovered by lavage are expressed as a percentage of the total cells recovered excluding red blood cells and epithelial cells), and as the total numbers of each cell type recovered. The remaining BAL fluid is centrifuged at 500 g 4° C. for 15 min. Aliquots of the supernate not immediately processed are stored at −80° C.

Effect of supplementation on eosinophil eicosanoid biosynthesis. 75 ml from a peripheral vein is collected 30 to 60 min prior to inhaled challenge and 24 h after challenge. Eosinophils are isolated as described in above. Cells are challenged with A23187 (1 μM) and PAF (1 μM). Leukotrienes are quantified after reverse phase HPLC as described above. Quantities of free fatty acid and prostaglandins are determined by NICI GC/MS.

Urinary $LTE_4$: Urine is collected for 3 h beginning immediately after antigen challenge and again from 3 h until after the LAR Urinary $LTE_4$ is measured using an RIA as described above.

Arachidonic acid release: Free fatty acid levels including AA in BAL, are determined, after addition of $^2H_3$-stearidonic acid and $^2H_8$-AA to BAL as internal standards, by NICI-GC/MS.

Example 2

In Vivo Studies Examining GLA Supplementation In Humans

About four years ago, the inventor's laboratory began to examine the influence of dietary GLA on AA metabolism in humans.

Incorporation of supplemented fatty acids into serum lipids

Initial studies examined the effect of dietary supplementation with GLA on the fatty acid content of serum lipids. Here 9 healthy adult volunteers consumed a controlled eucaloric diet consisting of 25% fat, 55% carbohydrate and 20% protein prepared in the metabolic kitchen of the GCRC.

Four menus were served on a rotating basis throughout the study period. In addition, three groups of three volunteers supplemented this diet with three different doses of GLA.

Figure 2:
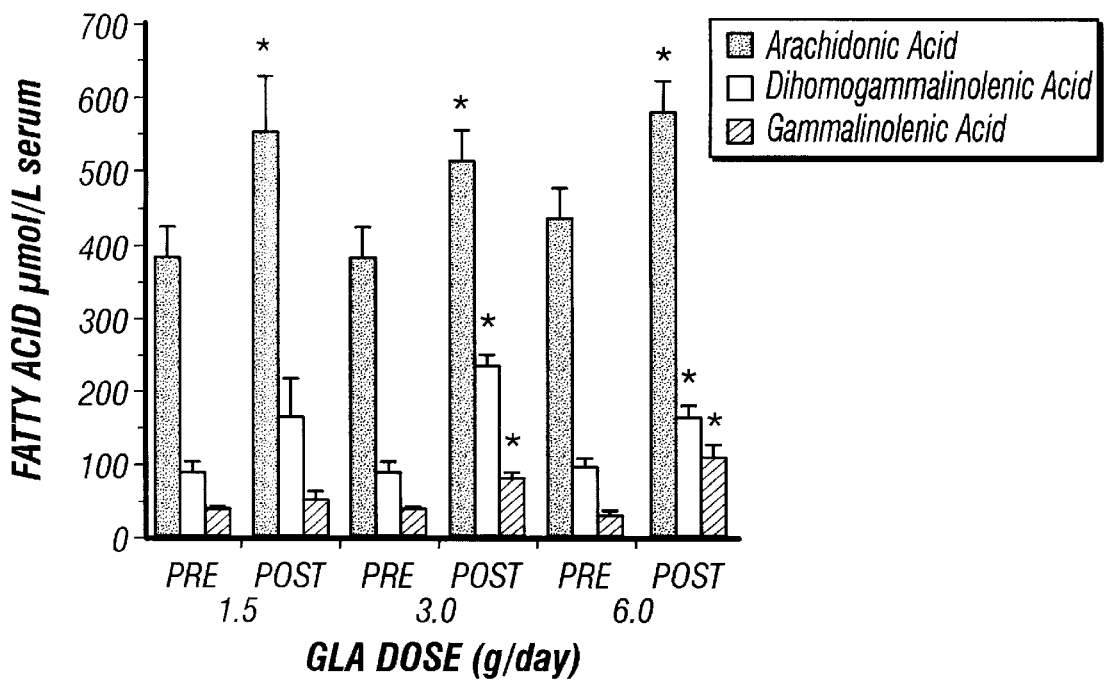
FIG. 2. Dose-response of GLA supplementation on serum fatty acid levels.

FIG. 2 demonstrates the effect of GLA supplementation at three different doses on serum levels of GLA, DGLA, and AA. In all three groups of subjects, AA significantly increased in serum lipids at the end of the three-week dietary period when compared with baseline values. Both GLA and DGLA significantly increased in the groups receiving 3.0 g/day and 6.0 g/day. In the two highest dose groups, DGLA levels increased two-fold and AA levels increased approximately 30% when compared to baseline values of these fatty acids in the same subjects. There was no significant change in serum fatty acid levels of volunteers eating control (25% energy as fat) diets, but not receiving the GLA supplement.

Figure 3:
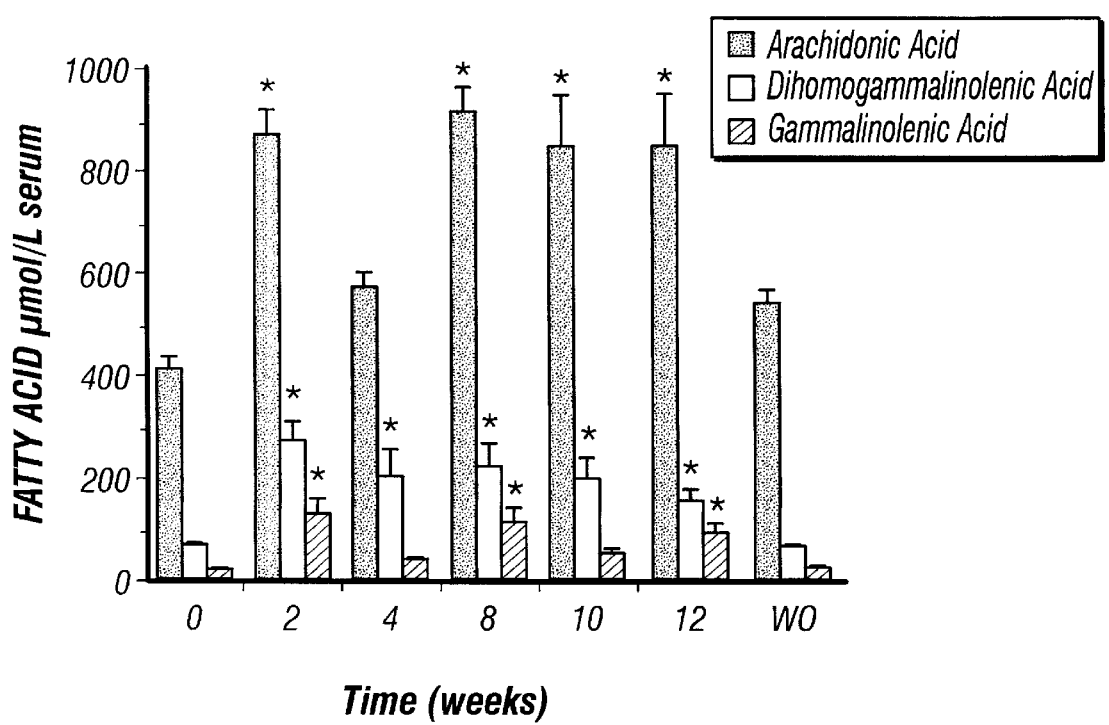
FIG. 3. Effect of GLA supplementation (up to 12 weeks) on fatty acid levels in human serum.

An important difference between the aforementioned studies and most clinical trials in the literature was the length of time of supplementation. Therefore, a long-term supplementation study (3.0 g/day) was performed over a 12-week period to assess whether fatty acid ratios and distribution would change in a manner that was not observed at three weeks. This study showed that there was a significant increase in serum GLA, DGLA. and AA levels by two weeks and that these levels stayed high over an additional 10 weeks of supplementation (FIG. 3). Taken together these data suggest that although some dietary GLA remains in the serum unchanged, substantial quantities of the elongation product (DGLA) and the elongation/$\Delta^5$-desaturase product (AA), accumulate in serum after GLA supplementation.

The next set of studies were designed to determine the distribution of supplemented fatty acids or their metabolites within individual glycerolipid classes of serum. Serum was collected from volunteers before and after receiving 6.0 g/day of GLA. Serum glycerolipids were separated by TLC and fractions were analyzed for fatty acid content following base hydrolysis by NICI-GC/MS. GLA was located predominately in triglycerides (36–38% of total), phospholipids (26–33% of total), and cholesterol esters (17–21% of total). After supplementation, GLA significantly increased in both phospholipids and cholesterol esters. In contrast, DGLA and AA were almost exclusively located in serum phospholipids, with very little of these fatty acids found in other serum pools. After supplementation, both DGLA and AA increased only in phospholipid pools.

Incorporation of supplemented fatty acids into neutrophil lipids

Figure 4:
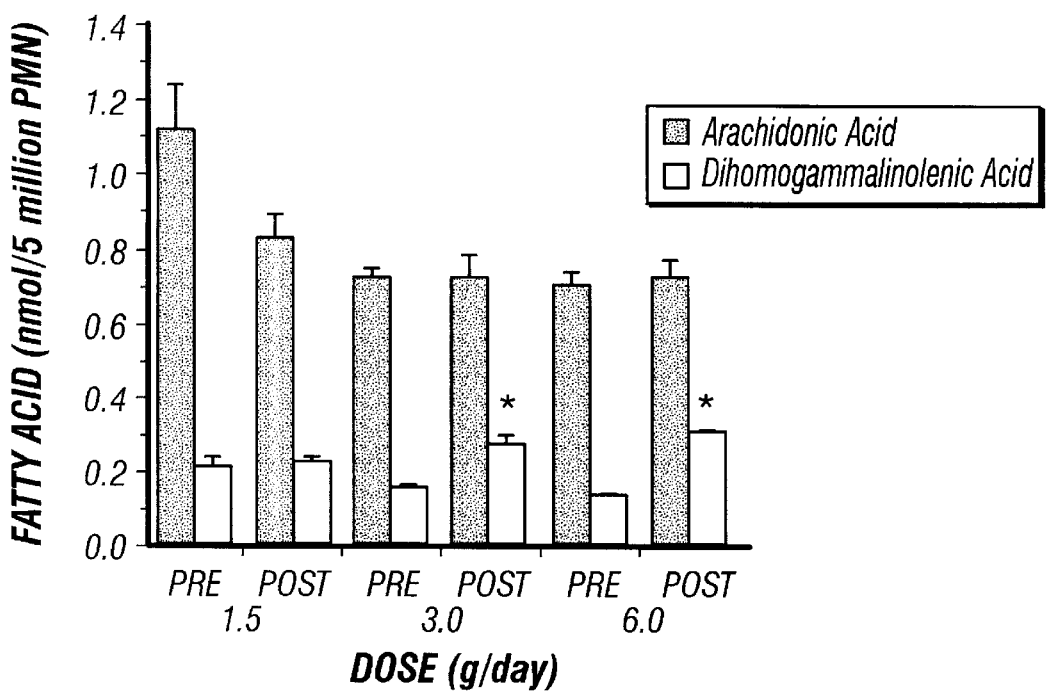
FIG. 4. Dose-response of GLA and metabolites supplementation into neutrophil lipids.

The fatty acid composition of the neutrophil lipids in subjects eating a controlled diet supplemented with 1.5, 3.0, or 6.0 g/day of GLA were also analyzed. No consistently detectable amounts of GLA were found in the glycerolipids of neutrophils before or after supplementation. Although relatively large quantities of AA were found in unsupplemented neutrophils, there was no significant change in AA within glycerolipids after supplementation at any of the doses given (FIG. 4). In contrast, DGLA within glycerolipids increased as a function of the dose provided to the volunteers. The AA/DGLA ratio decreased from approximately 5.4:1 before supplementation to 2.3:1 three weeks after 6.0 g/day of GLA supplementation. There was no significant change in fatty acid levels in control subjects eating the study diet without supplementation. These findings suggest that neutrophils rapidly elongate GLA to DGLA but lack the ability to desaturate DGLA to AA.

Figure 5:
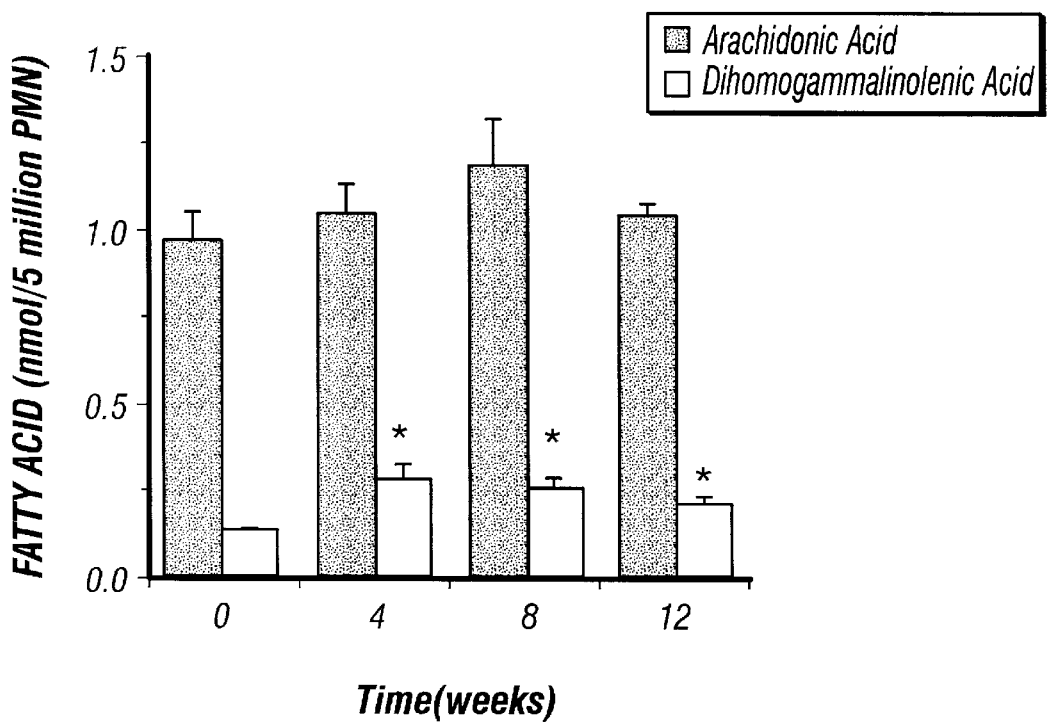
FIG. 5. Effect of GLA supplementation (up to 12 weeks) on fatty acid levels in human neutrophils.

The influence of long term (12 week) GLA supplementation (3 g/day) on the composition of GLA, DGLA and AA in neutrophil lipids also was examined. In contrast to serum, GLA supplementation resulted in an increase in DGLA but not AA even at 12 weeks (FIG. 5). It is not clear why the increase of AA in serum is not eventually observed in neutrophil lipids; perhaps this AA is in a serum pool not available to neutrophils. Taken together these preliminary data indicate that GLA provided as a dietary supplement is converted to different products (DGLA in inflammatory cells and AA in serum) depending on where it is metabolized. This results in the potentially beneficial effect of reducing AA metabolism in inflammatory cells balanced against the potential adverse effects of the accumulation of serum AA levels. These studies led to studies designed to determine whether it is possible to utilize the endogenous elongase activity within inflammatory cells to synthesize analogs of AA from appropriate dietary precursors without concomitantly increasing levels of circulating AA.

Figure 6A:
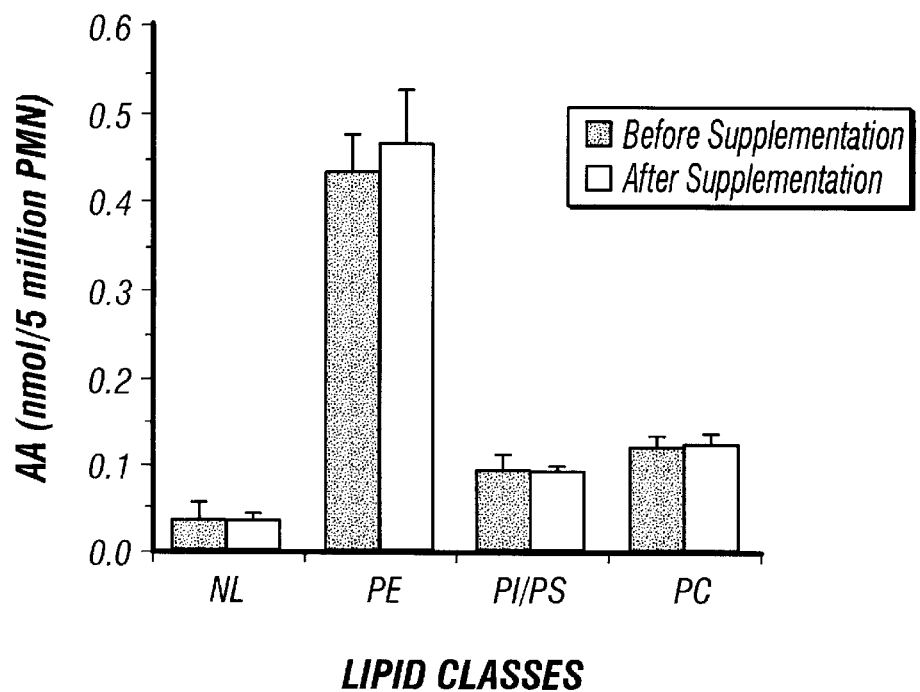
FIG. 6A and FIG. 6B. Incorporation of AA (FIG. 6A) and DGLA (FIG. 6B) into glycerolipid classes of neutrophils.
Figure 6B:
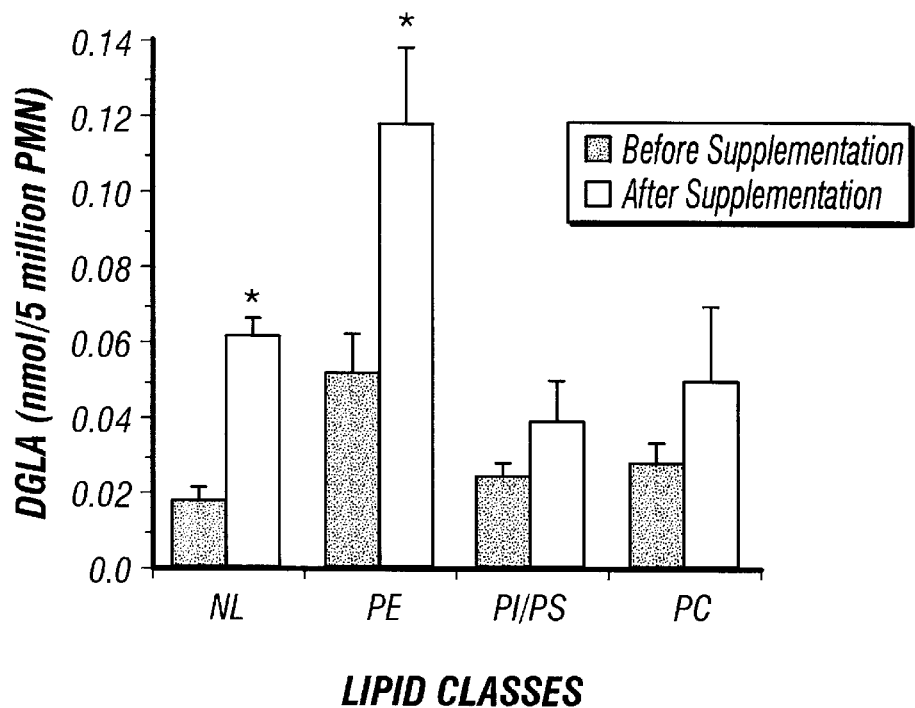

To better determine the distribution of fatty acids within different glycerolipid classes, neutrophils were obtained before and after supplementation with 6.0 g/day of GLA for 3 weeks and glycerolipids were separated by normal phase HPLC. Quantities of fatty acids in each glycerolipid class were then determined by NICI-GC/MS. As shown in FIG. 6A, the majority of AA (>60%) within the neutrophil lipids was located in phosphatidylethanolamine (PE) and neither the absolute amount nor its relative distribution changed significantly after dietary supplementation with GLA. Similarly, the bulk of DGLA in the neutrophil was associated with PE (40%) (FIG. 6B). There were significant increases in the amount of DGLA associated with both PE and neutral lipids after supplementation, For example, the AA/DGLA ratio in PE decreased from 8.3:1 before supplementation to 4:1 after supplementation. These data illustrate that AA and DGLA reside in similar glycerolipid pools both before and after supplementation.

Figure 7:
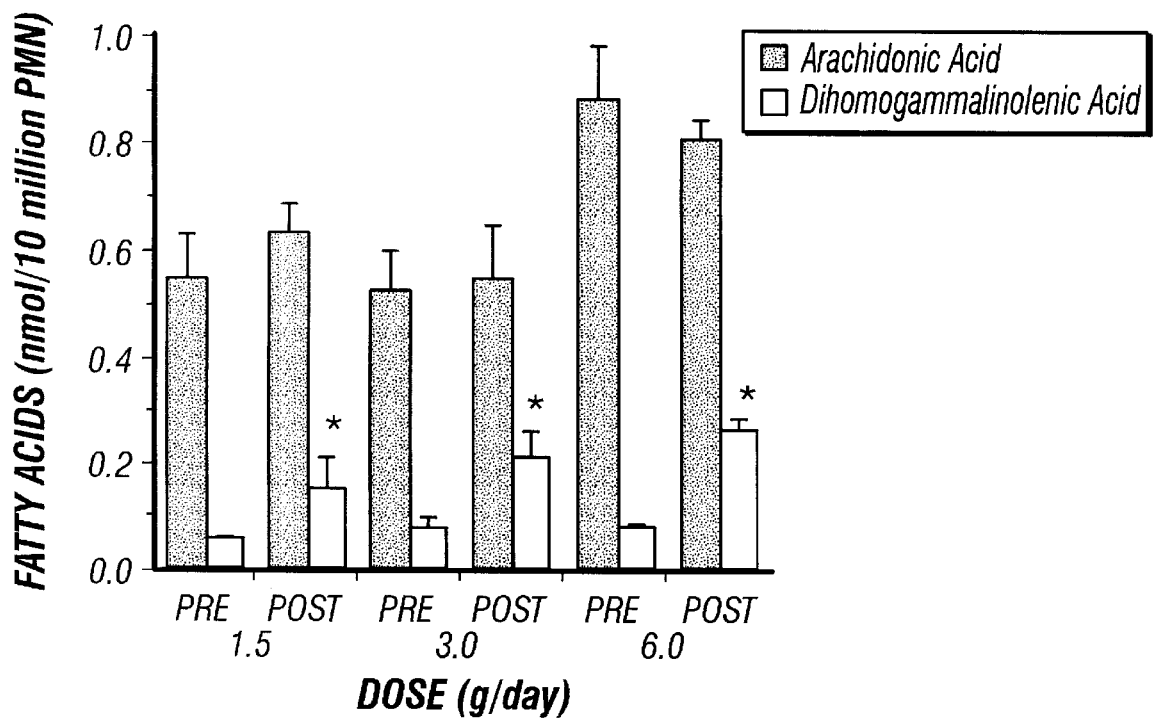
FIG. 7. Fatty acid release from stimulated neutrophils before and after supplementation.

Influence of GLA supplementation on the release of fatty acids or the production of lipid mediators by stimulated neutrophils Neutrophils were next obtained from subjects before and after supplementation and stimulated with ionophore A23187. The release of AA from the neutrophil glycerolipids after stimulation did not change following supplementation. However, the release of DGLA increased by 63%, 65%, and 69% in those volunteers receiving 1.5 g, 3.0 g and 6.0 g/day GLA, respectively (FIG. 7). These data support the hypothesis that the fatty acid composition of the neutrophil glycerolipids impacts on the fatty acids released upon cellular stimulation. They also suggest that the $PLA_2$ isotype(s) enzyme responsible for mobilizing fatty acids hydrolyzes DGLA in addition to AA.

Figure 8:
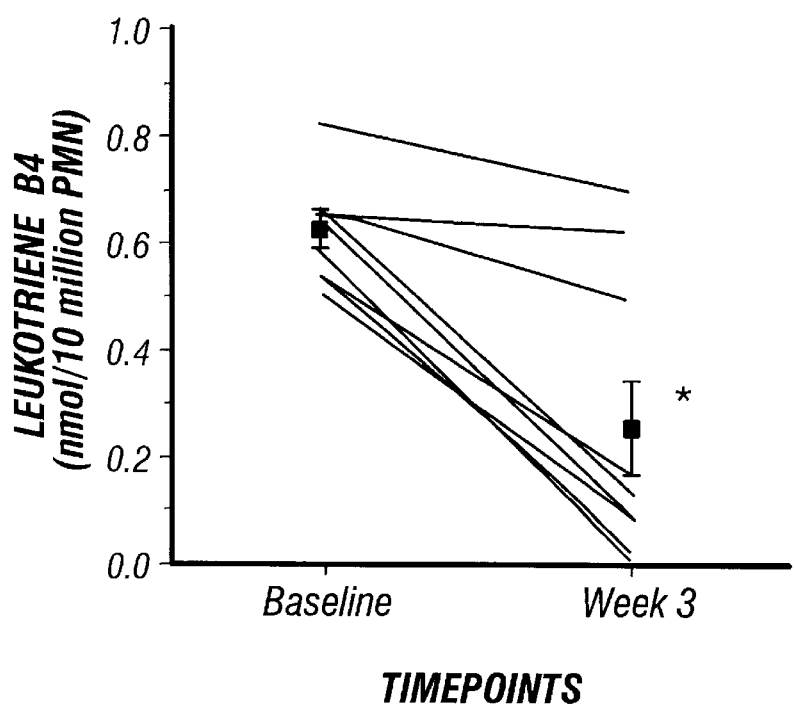
FIG. 8. Influence of GLA supplementation on leukotriene generation.
Figure 9:
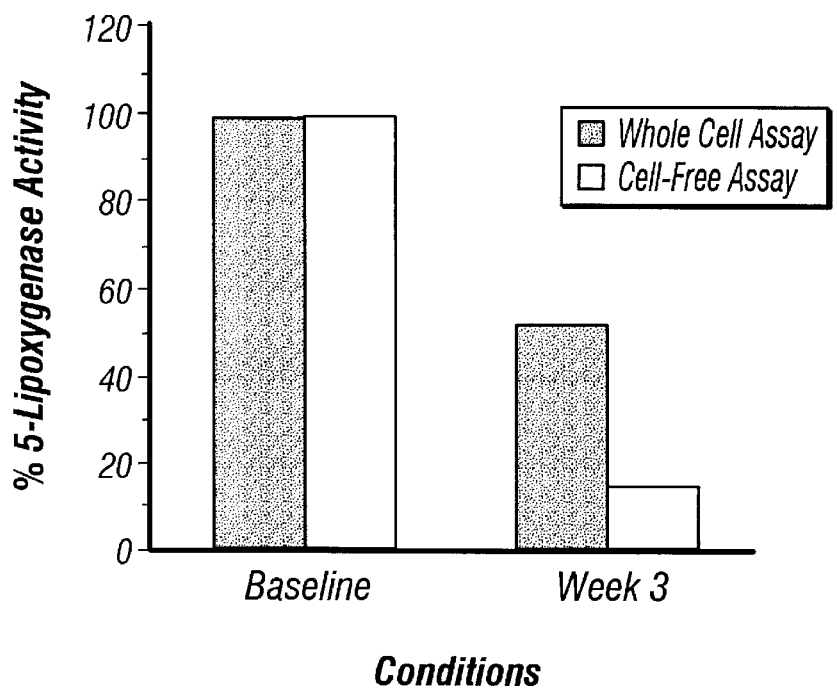
FIG. 9. Influence of GLA supplementation on 5-lipoxygenase activity.

While the aforementioned studies demonstrated that GLA supplementation did not influence the ex vivo release of AA from neutrophil glycerolipids, it was unclear whether GLA supplementation would alter leukotriene biosynthesis. To examine this question, neutrophils were stimulated and the synthesis of $LTB_4$, 20-OH $LTB_4$, and the 6 trans isomers of $LTB_4$ were measured by reverse phase HPLC analysis. Neutrophils from subjects supplementing their controlled diets with 3.0 g/day GLA produced 60% less $LTB_4$ than the same subjects before supplementation (FIG. 8). 20-OH $LTB_4$, 6-trans $LTB_4$ and 6-trans 12-epi $LTB_4$ levels were decreased to a similar degree after supplementation.

A final set of studies measured changes in the capacity of neutrophils to generate PAF ex vivo before and after GLA supplementation. Neutrophils of subjects receiving 3.0 g/day of GLA produced 40% less PAF after supplementation than neutrophil obtained from those same subjects before supplementation. Taken together, these data reveal that GLA supplementation can alter the capacity of neutrophils to generate lipid mediators. This inhibition appears to occur at some step distal to the phospholipase-catalyzed cleavage of AA from membrane phospholipids.

Example 3

In Vitro Studies Examining The Metabolism Of GLA In Human Neutrophils

Figure 10:
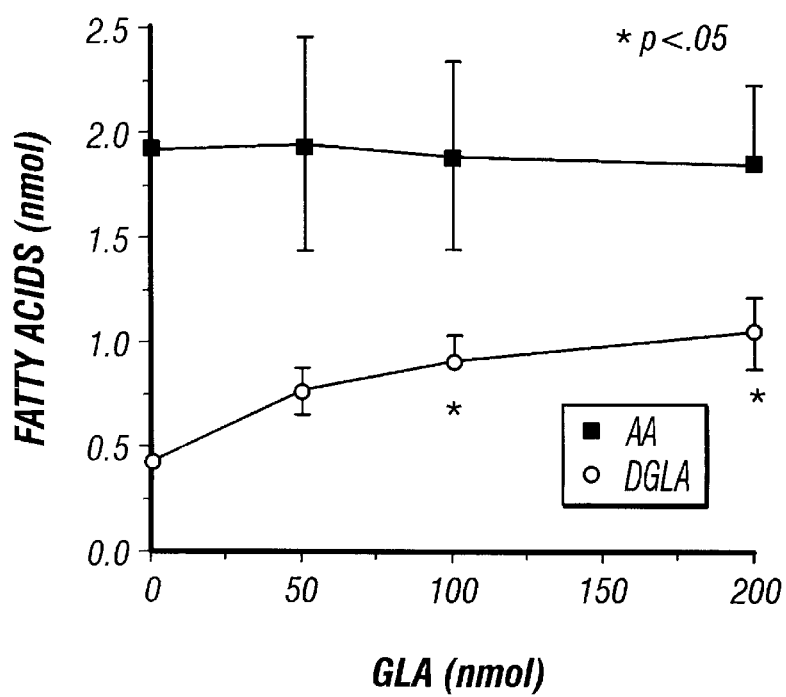
FIG. 10. In vitro metabolism of GLA in human neutrophils.

It is generally assumed that the liver has a key role in the in vivo elongation and desaturation of n-6 fatty acids. However, the role of other cells (especially inflammatory cells) and tissues has not been extensively studied. In addition, it is critical to evaluate the mechanism of leukotrienes inhibition in less complex (than in vivo model) systems. To begin to address these problems, the inventor developed a model in which neutrophils could be incubated long-term with fatty acids or other fatty acid derivatives. Human neutrophils have been isolated and cultured overnight in RPMI, 2% insulin-transferrin and fetal bovine serum (FBS). In initial studies, varying concentrations of GLA (complexed to albumin) were provided to these cultured neutrophils for 24 h. FIG. 10 shows quantities of DGLA and AA in neutrophils at increasing concentrations of GLA. The quantity of DGLA in neutrophil glycerolipids increased as a function of the concentration of GLA. In contrast, there was no change in the quantity of AA in neutrophil phospholipids. These data revealed that neutrophils have the capacity to take up GLA and rapidly elongate it to DGLA. However, they do not desaturate DGLA to form AA. These data are consistent with in vivo findings that indicate that GLA supplementation leads to an increase in DGLA, but not GLA or AA in human neutrophil glycerolipid. Furthermore, they provide direct evidence that the neutrophil themselves can elongate GLA in vivo.

Figure 11:
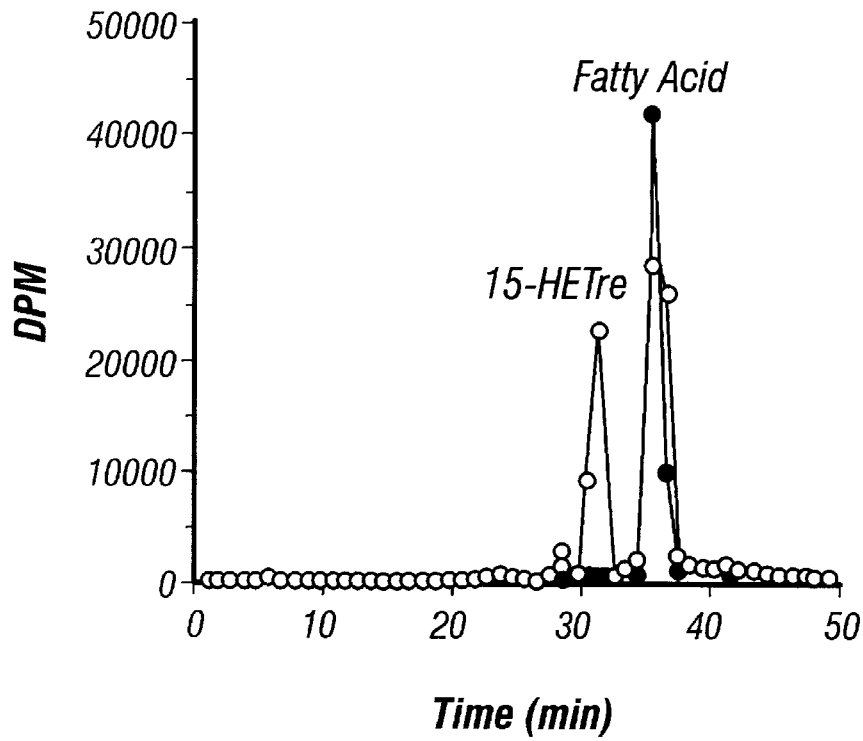
FIG. 11. Metabolism of $^{14}$C-DGLA to products by stimulated neutrophils.

It has been long recognized that arachidonate is hydrolyzed by phospholipase $A_2$ isotypes from membrane glycerolipids by lipases during cell stimulation. However, to date, there is little direct evidence that similar mechanisms exist to mobilize DGLA. To examine this question, neutrophils that had been cultured with varying concentrations of GLA (0 to 200 nmol) were stimulated with ionophore A23187, and mobilized fatty acids were measured by NICI GC/MS. In contrast, DGLA along with AA were released from neutrophils during stimulation. To determine if neutrophils can further metabolize DGLA to oxygenated products, stimulated cells were provided [$^{14}$C]-DGLA and products were measured by reverse HPLC. Neutrophils primed with LPS followed by stimulation with FMLP also converted DGLA to 15 HETrE. FIG. 11 illustrates that A23187 stimulated neutrophils produce a labeled product that migrated with 15-HETrE. In contrast, none of this product was observed in unstimulated cells. To the inventor's knowledge, these are the first studies to demonstrate the capacity of neutrophils to release DGLA and convert it into oxygenated products. At this point in time, it is very important to unambiguously identify this oxygenated product Although it migrates with 15-HETrE by reverse phase HPLC, other monooxygenated products can migrate near this product.

Figure 12:
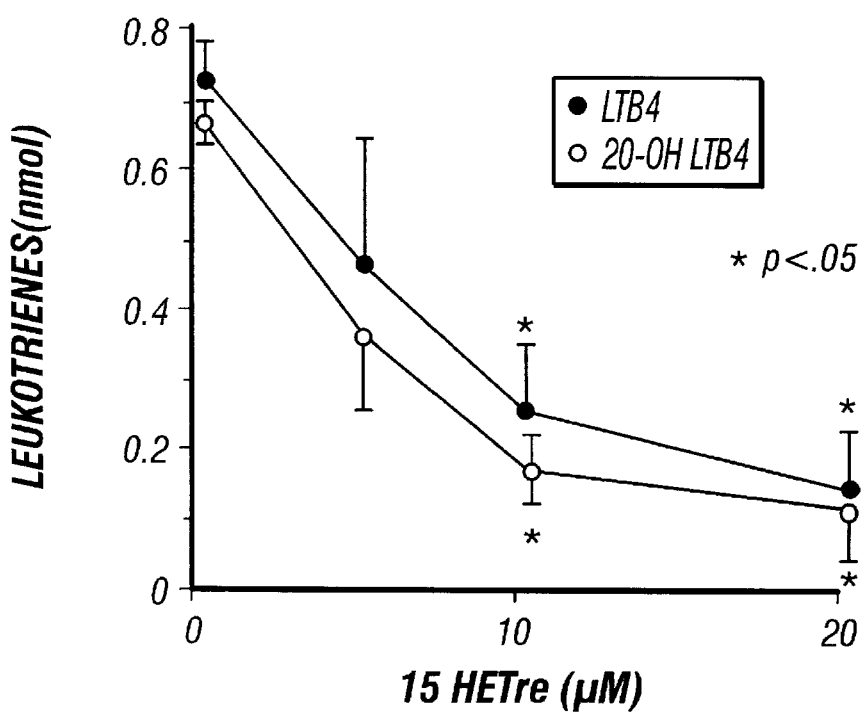
FIG. 12. Influence of 15-HETrE on leukotriene generation.

In particular, the inventor is interested to determine if the neutrophil can also produce 8-hydroxy-9,11,14 eicosapentaenoic acid from DGLA. Borgeat and colleagues reported this to be a product of the incubation of dihomogammalinolenic acid with rabbit neutrophils. Studies were also designed to examine whether 15-HETrE produced by neutrophils might influence $LTB_4$ generation. Previous studies by Vanderhoek and colleagues have demonstrated that the AA product, 15-HETE, can reduce 5-lipoxygenase activity (Vanderhoek et al., 1980). Neutrophils were isolated from normal unsupplemented volunteers and were treated with various concentrations of 15-HETrE and then stimulated with ionophore A23187. FIG. 12 shows the generation of $LTB_4$ and its major metabolite 20-OH $LTB_4$ by stimulated neutrophils. 15-HETrE induced a dose-dependent inhibition of leukotriene generation with an $IC_{50}$ of approximately 5 µM. In addition, DGLA at higher concentrations ($IC_{50}$, ~10 µM) also inhibited leukotriene generation. Although these studies do not prove that 15-HETrE or DGLA is the in vivo inhibitor of 5-lipoxygenase, they reveal that DGLA and oxygenated products of DGLA can potently influence eicosanoid generation.

Example 4

Influence Of The Combination Of GLA And Eicosapentaenoic Acid (EPA) On The Fatty Acid Composition Of Serum And Neutrophil Lipids.

Figure 13:
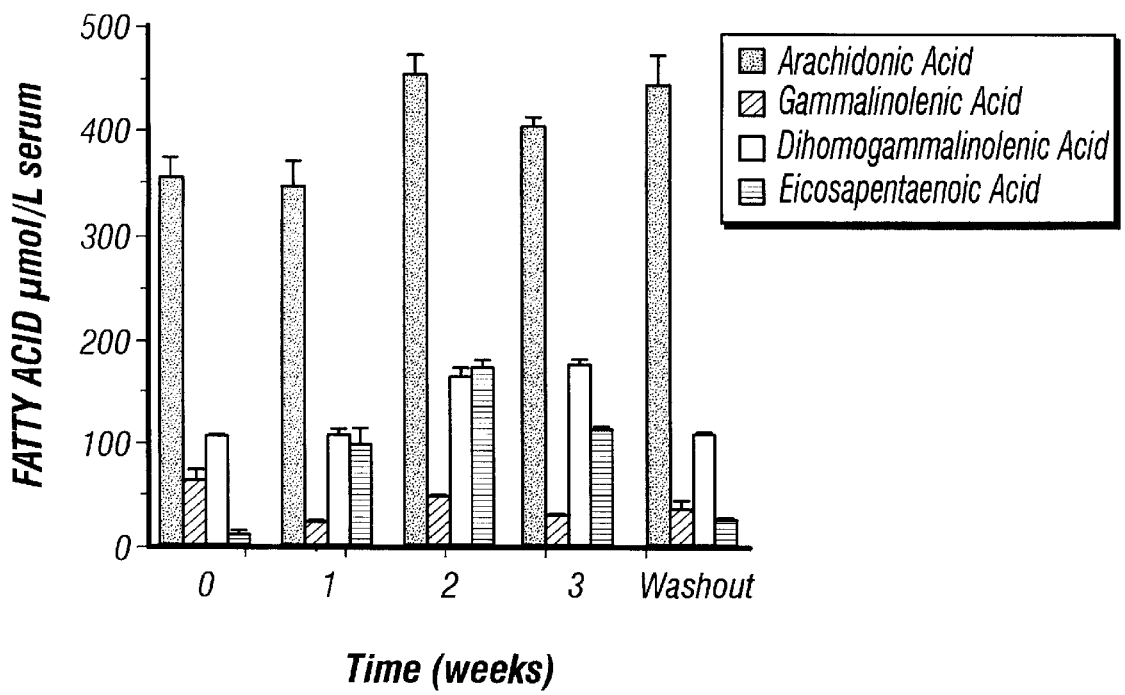
FIG. 13. In vitro metabolism of stearidonic acid in human neutrophils.

As mentioned above, a concern with the long-term effects of GLA supplementation is that there is an increase in serum levels of AA. Therefore there is a need to find dietary strategies which will produce natural antagonist of AA in inflammatory cells without increasing serum AA. Previous in vitro studies in isolated hepatocytes and in vivo studies in animals suggest that EPA is a product inhibitor of the $\Delta^5$ desaturase (Gronn et al., 1992, Dang et al., 1989). In order to determine whether EPA would perform a similar function in humans in vivo, three subjects on control diets (25% fat) were supplemented with a combination of EPA (1.5 g/day) and GLA (3.0 g/day) for three weeks. The inventor showed (FIG. 4 and FIG. 5) that this quantity of GLA (alone) induces marked increases in serum AA in both the short (3 weeks) and long term (12 weeks). The combination of GLA and EPA resulted in marked increases in GLA, DGLA and EPA in serum lipids. However, in contrast to the GLA supplementation alone, the combination of EPA with GLA did not cause an increase in serum AA (FIG. 13). These interesting results suggest that it may be possible to block the $\Delta^5$ desaturase in humans with EPA thereby providing a means to supplement humans with high levels of GLA without concomitant increases in serum AA levels.

Example 5

Figure 1:
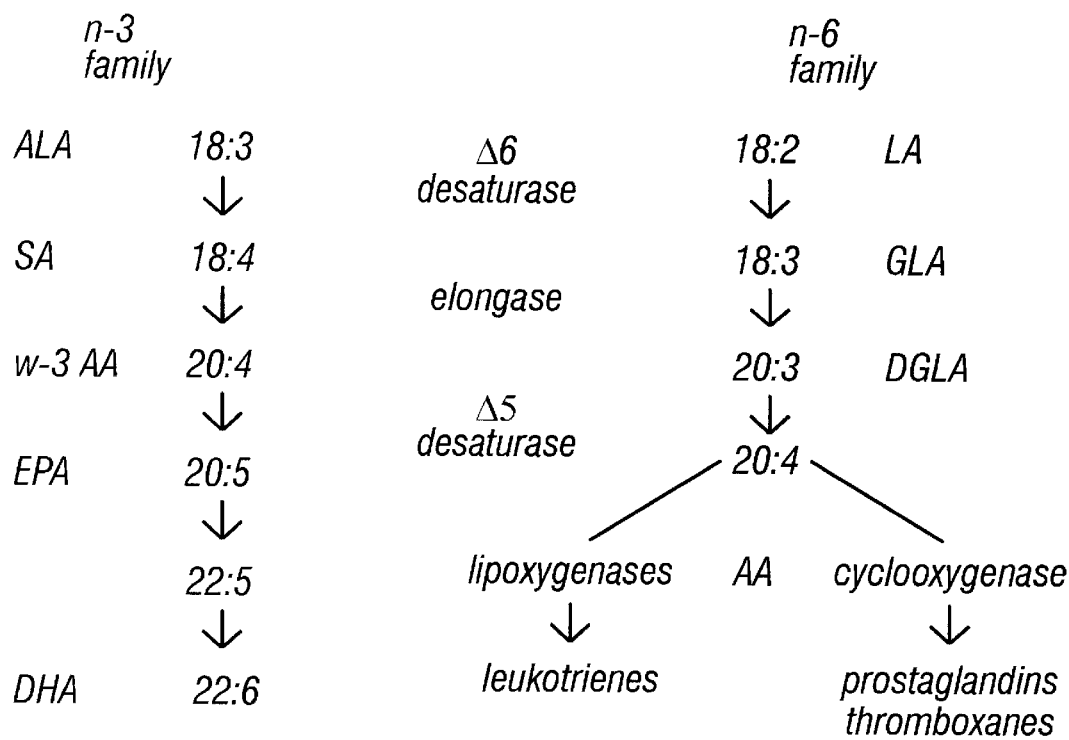
FIG. 1. Biochemical desaturation/elongation of essential fatty acids to polyunsaturated fatty acids.
Figure 14:
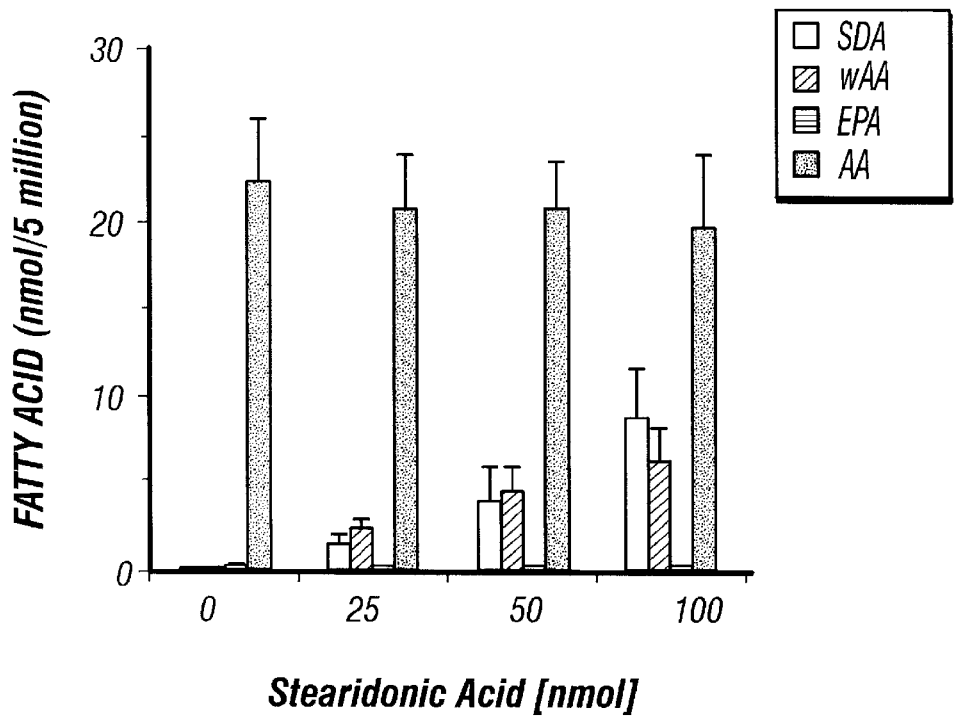
FIG. 14. In vitro metabolism of stearidonic acid in human neutrophils.

In vitro studies examining the metabolism of stearidonic acid in human neutrophils The inventor has shown above that human neutrophils (in vitro in overnight culture) will take up GLA and elongate it to DGLA but not further desaturate that DGLA to AA. An alternative route to depeleting AA in neutrophils may also be useful in modulating the inflammatory responses mediated by AA and its metabolites. The inventor hypothesized, therefore, that the n-3 fatty acid, stearidonic acid (18:4) would also be elongated in neutrophils to form ω-3 arachidonic acid (FIG. 1). To test this hypothesis, varying concentrations of stearidonic acid were provided to cultured neutrophils for 24 h. Lipids were extracted and the quantities of fatty acids determined after base hydrolysis using GC/MS. There was no detectable ω-3 arachidonic acid in neutrophils before supplementation (FIG. 14). However, addition of stearidonic acid caused a dose-dependent increase in ω-3 arachidonic acid in glycerolipids of these cells. In contrast to this increase, there was no increase in the $\Delta^5$ desaturase product of ω-3 arachidonic acid, eicosapentaenoic acid or AA. Analogous to supplementation with GLA, these data reveal that neutrophils have the capacity to take up stearidonic acid and rapidly elongate it to ω-3 arachidonic acid. However, they do not further desaturate ω-3 arachidonic acid to form eicosapentaenoic acid.

These studies raise the interesting possibility that high levels of the AA analog, ω-3 AA, can be induced in inflammatory cells by providing inflammatory cells (in vitro or in vivo) with stearidonic acid. Moreover, they point out the potential for ω-3 AA to compete with natural AA (n-6) for enzymes (phospholipase $A_2$ isotypes, cyclooxygenase isotypes, and 5-lipoxygenase) that convert AA to oxygenated metabolites.

Example 6

Development Of A Model To Study The Influence Of Diet On Clinical And Biochemical Parameters Of Asthma Asthma presents a defined inflammatory disease that can be used as a model to test the efficacy of dietary manipulation. To this end an asthma model in humans was developed to test the reproducibility of the in vitro data and to determine the best dietary strategies. Another benefit of such a model is it allows the investigator to establish the effect of antigen challenge on AA levels in bronchoalveolar lavage fluid (BALF). Thus the present example teaches the use of an asthmatic model to test these parameters To this end, measures of airway physiology, and analysis of BALI- cellular and biochemical constituents were obtained from 5 stable atopic asthmatics before and after antigen challenge both with and without prior corticosteroid therapy. A systemic corticosteroid arm was felt to be impost to validate the physiologic variables as well as to ascertain which components in the BALF were sensitive markers of steroid-responsive inflammation. Additionally, AA levels were measured in BALF 4 h after inhaled antigen challenge (7 subjects) and at the time of the LAR (5 subjects). For comparison, identical BALF analyses were performed in ten normal volunteers (without antigen challenge or corticosteroids).

Methods

Study Design

Asthmatic subjects were defined using criteria proposed by the American Thoracic Society (1987). Normal subjects were healthy non-smokers, without respiratory symptoms. In all subjects, demographic data, history and physical examination, baseline spirometry, skin testing and methacholine PC20, using a tidal breathing technique, were obtained after informed consent for study participation. This was followed, no earlier than 7 days later, by baseline bronchoscopy for collection of BALF. This concluded the study protocol for normal subjects.

In 5 subjects, inhaled antigen challenge was performed using a previously described protocol and physiologic data collected. Not less than 2 weeks later, PC20 was again determined and antigen challenge repeated with BALF collected at the time of the LAR as determined during the first challenge. Two to 4 weeks later, these subjects were placed on 40 mg of prednisone daily for 7 days. Inhaled antigen challenge was again performed and BALF obtained at the same time after antigen challenge as on the previous visit. In additional 7 subjects, BALF was obtained 4 h after inhaled antigen challenge, but without a subsequent course of prednisone therapy.

Statistical analysis

In the asthmatic patients, the changes in cell composition, eosinophil cationic protein (ECP), and protein in BALF among study conditions were examined using one way ANOVA with study period as the independent variable. If a significant interaction was found, a paired t-test was used to compare the means among test periods. Because the AA levels were not normally distributed within the groups, the non-parametric Wilcoxon signed-ranks test was used to analyze the differences in these measurements. A $p<0.05$ was used to determine statistical significance.

Results

Measures of airway response to antigen challenge were consistent and reproducible both immediately and at LAR. The mean time for LAR, was 6.4±1.5 h after challenge. The mean (±SD) fall in $FEV_1$ immediately after antigen challenge was 35±8% while the fall at LAR was 28±18% from baseline $FEV_1$ Following prednisone, both the immediate response and LAR were ablated.

The percentages of neutrophils and eosinophils in BALF were significantly higher in the asthmatics. The level of ECP rose after antigen challenge and was suppressed by corticosteroid administration (p=0.03). While the percentage of eosinophils tended to mirror the changes in ECP, these changes did not achieve statistical significance. AA levels in BALF rose after antigen challenge (mean±SE: baseline= 2.2±0.3 ng/ml BALF; post-challenge=3.9±1.0; p<0.05).

Discussion

This antigen challenge model of asthma provides reproducible physiologic (pulmonary function) data within and between subjects. Further, ECP appears to be a reproducible surrogate measure of eosinophil presence and/or activity in this model. In addition, AA levels can be observed to increase after antigen challenge in this model. Collectively, these measures offer the capability of assessing the efficacy of dietary manipulation with the expectation that significant differences among treatment regimens can be detected with a relatively small number of study subjects.

Example 7

Effect of GLA supplementation on eosinophil fatty acid composition and airway functions.

Figure 15:
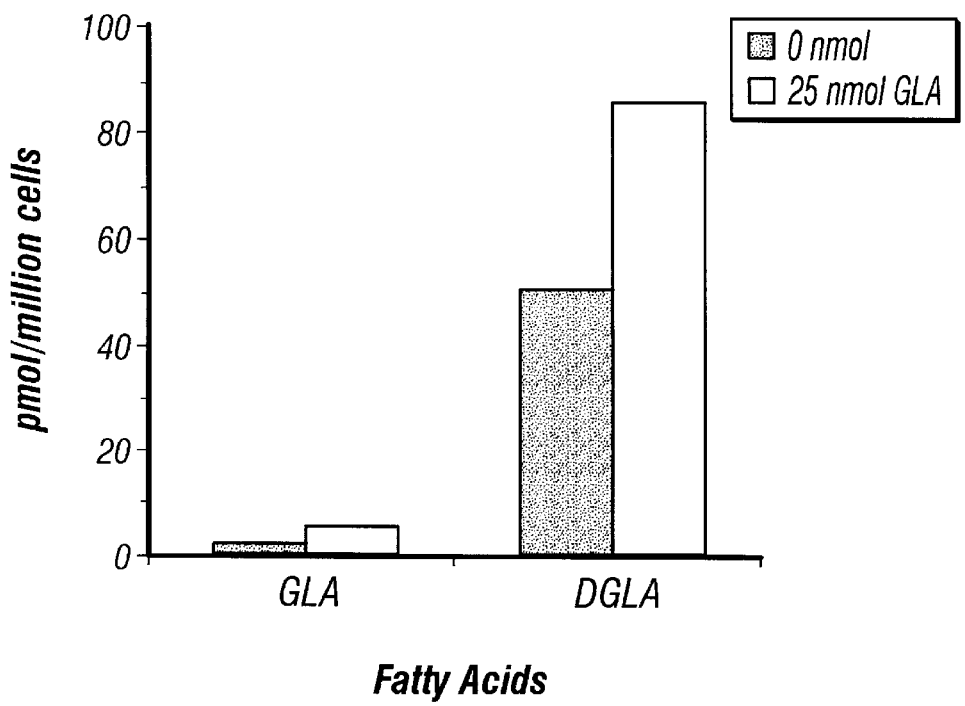
FIG. 15. Metabolism of GLA by human eosinophils

An issue with the GLA preliminary data obtained thus far with neutrophils is its relationship to atopic asthma and in particular whether the neutrophil has a key role in atopic asthma. While there is evidence that the neutrophil has a role in atopic asthma, previous studies, to date, point to the eosinophil as having a central role. Therefore it was important to determine how GLA was metabolized by human eosinophils. Thus, eosinophils were isolated from atopic subjects and incubated with GLA as described above. Like the human neutrophils, supplementation of human eosinophils resulted in a marked increase in DGLA but no change in the quantity of AA in eosinophil glycerolipids (FIG. 15). These data reveal that eosinophils have the capacity to take up GLA and rapidly elongate it to DGLA. However, eosinophils do not further desaturate DGLA to form AA.

Figure 16:
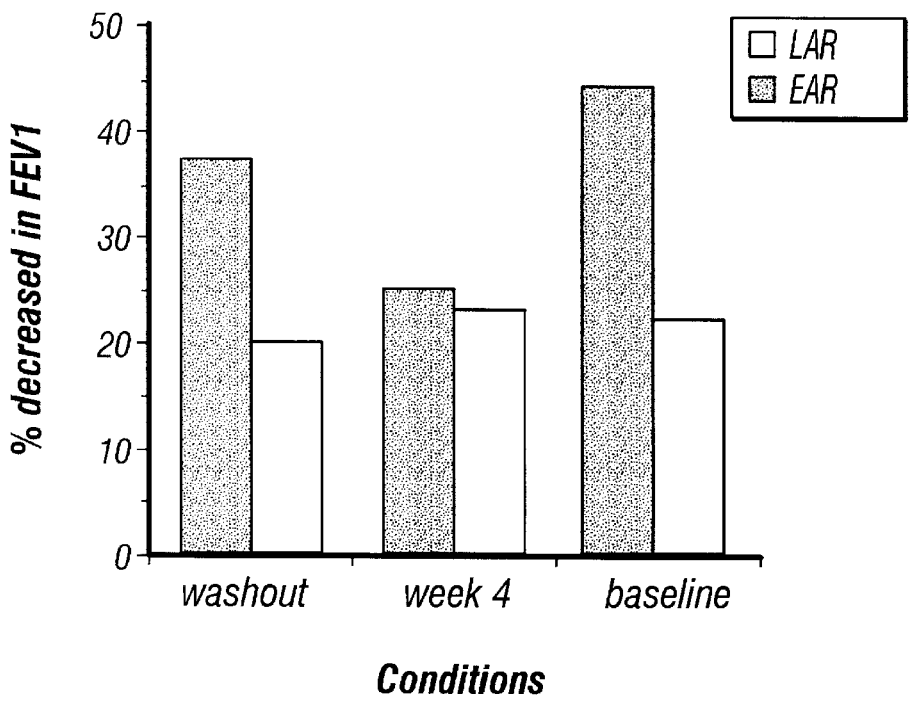
FIG. 16. Influence of borage oil on early and late asthmatic response.

In a second set of studies, two atopic asthmatics were recruited and challenged with antigens as described above. In both subjects, the concentration of antigen necessary to drop $FEV_1$ by greater than 20% was established. At a subsequent date, they were each challenged with these respective concentrations of antigen and they were each monitored with spirometry to assess the development of an early and late response. Each of these subjects were then placed on GLA supplementation for four weeks and then challenged again with the same dose of antigen. The subjects were then placed back on their normal diets for two weeks and then challenged again with the same respective dose of antigen. FIG. 16 shows the average of the responses of the two subjects at the three challenge periods. The magnitude of the early response was diminished (when compared to pre and post GLA supplementation) in both subjects four weeks after GLA supplementation. In contrast, GLA supplementation did not influence the late response.

Additionally, the influence of GLA supplementation in a human model of atopic asthma, on eicosanoid production, bronchial reactivity and airway cellular influx can be measured as detailed herein. A random order, placebo-controlled crossover design preceded by a control diet "run in" phase study is performed. A crossover design is chosen to keep the number of subjects required for statistical validity as small as possible by minimizing the influence of intersubject variability with regards to the severity of asthma, environmental triggers and exposures, and nature and severity of the late asthmatic response (LAR). Subjects are studied after 3 weeks of a controlled "normal" diet with 25% of calories from fat, after 3 weeks of the "experimental" diet consisting of the "normal" diet supplemented with 4.5 grams (15 capsules/day) of GLA as borage oil, and after 3 weeks of a "placebo" diet consisting of the "normal" diet with 4.5 grams (15 capsules/day) of olive oil. Olive oil is 70% oleic acid, 13% C16 and 15% C18 (<1%, n-3) fatty acids as triglycerides. Neither oil supplement has either an odor or a taste when in capsule form. The experimental and placebo diets are given in random order. Each 3 week period is separated by a 4–6 week usual diet "washout" period when the diet of the study subjects is not controlled. Preliminary data from this group suggests that 4 weeks is a sufficient time period for abolition of an effect of diet during the preceding study period.

Results

The inventor postulates that GLA supplementation and not placebo or "normal" diets will mitigate the response to antigen challenge as measured by the decrements in $FEV_1$ both immediate and the LAR, and reduce the influx of eosinophils into airways during the LAR. GLA supplementation will also likely attenuate antigen-induced urinary $LTE_4$ exertion and BALF AA increases.

While the antigen challenge model is capable of detecting a therapeutic effect due to prednisone with a small number of subjects, GLA supplementation may be associated with smaller, though significant, effects that are overlooked using relatively small sample sizes. The trial uses 10 subjects per group. Sample sizes are based on variance estimated and differences reported in the preliminary results. The contemplated sample sizes have a 90% power to demonstrate an effect on pulmonary function ($FEV_1$) that is at least half the magnitude observed with oral prednisone therapy in the pilot study, at an alpha of 0.05. Asthma is a complex disease process and it is possible that significant effects in some components may be missed by using, a model that is not sensitive to these effects. For example an antigen challenge model would not be the appropriate system in which to detect an impact on neurally-mediated immediate processes (e.g., airway cooling). The effect of GLA supplementation, would, however, suggest that this antigen challenge model is appropriate.

Example 8

Dietary Strategies in Humans Utilizing Endogenous Elongase Activity Within Inflammatory Cells to Synthesize Structural Analogs of AA from Dietary Precursors Without Concomitantly Increasing Levels of Circulating AA.

The data suggests there may be two strategies which can be utilized in humans to synthesize analogs of AA in inflammatory cells without concomitant increases in serum AA. The first approach (FIG. 17A) is to supplement the diets of humans with a combination of gammalinolenic acid (GLA) and eicosapentaenoic acid (EPA). This strategy is based on in vitro data in hepatocytes and in vivo data in animals which indicate that EPA is a product inhibitor of the enzyme activity that synthesizes it, the $\Delta^5$ desaturase (Gronn et al, 1992; Dang et al., 1989). The inventor has shown in two volunteers that administering of GLA in combination with EPA will induce a marked accumulation of DGLA in circulation and neutrophil lipids without causing a marked accumulation of AA in serum lipids (which is seen with GLA supplementation in the absence of EPA).

If in vivo administration of EPA is an effective means to block the hepatic $\Delta^5$ desaturase, this combination should furnish a means to provide high concentrations of GLA to humans to synthesize the close structural analog of AA, DGLA, in inflammatory cells thereby inhibiting AA metabolism, eicosanoid biosynthesis and attenuating signs and symptoms of inflammatory disorders, without the significant side effect of the accumulation of AA in circulation.

Figure 17B:
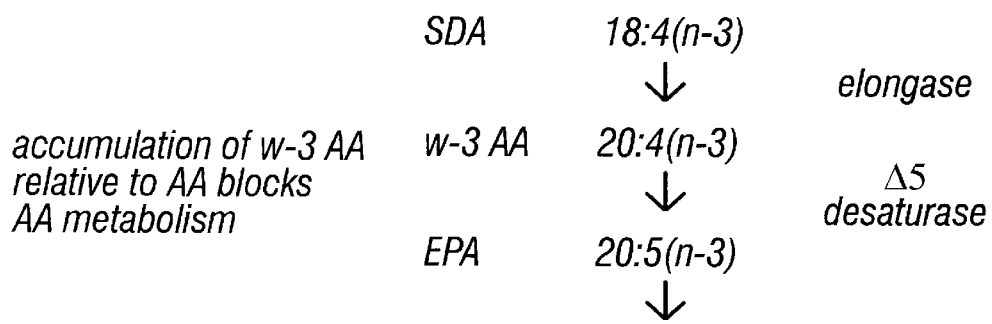

The second approach involves administering the n-3 fatty acid, stearidonic acid, to humans (FIG. 17B). This fatty acid is converted (by the endogenous elongase in inflammatory cells) to a structural analog of AA, ω-3 AA and this product will block AA metabolism and thus have anti-inflammatory effects. There have been several studies over the last few years which have examined the effects of in vivo supplementation with alpha linolenic acid (18:3, n-3) in both humans and animals. Generally, these studies have shown that alpha linolenic acid has only modest anti-inflammatory effects (Nordstrom et al., 1995; Larsson-Backstrom et al., 1995; Clark et al., 1995; Shoda et al., 1995). However, only a very small portion of alpha linolenic acid is converted to stearidonic acid by the $\Delta^6$ desaturase. In fact, this step appears to be the rate-limiting step in n-3 polyunsaturated fatty acid biosynthesis. The inventor's concept is that stearidonic acid supplementation is an efficacious means to block AA metabolism because it bypasses the rate-limiting step ($\Delta^6$ desaturase) and is directly utilized by inflammatory cell elongase activity. A major advantage of stearidonic acid versus GLA (alone) as a supplement is that the elongation/$\Delta^5$ desaturase product from this precursor is EPA and not AA. Consequently even if EPA accumulates in serum components, it will not have the potential detrimental effects of AA.

Example 9 in vivo Supplementation with a Combination of GLA and EPA

The present Example describes the effect of in vivo supplementation with a combination of GLA and EPA on the quantities and ratios of n-3 and n-6 polyunsaturated fatty acids in serum and neutrophil lipids and the ex vivo capacity of stimulated neutrophils to release fatty acids and produce eicosanoids.

Human dietary studies are particularly difficult to control because individuals have different starting levels of fatty acids based on their previous individual diets and metabolism. To limit this variability, three randomly assigned groups of volunteers (10 per group, 5 males and 5 females) are provided identical 25% fat diets for two weeks before starting fatty acid supplementation. Then one group of volunteers consumes 3.0 g/day GLA; another group consumes 1.5 g/day EPA and a third group consumes 3.0 g/day GLA and 1.5 g/day EPA. The concentrations of these supplements were determined based on previous studies in which the effects of dietary GLA or EPA, alone have been examined (Chilton et al., 1993: Johnson et al. 1997). All groups consume their respective supplements and identical controlled 25% fat diets for four weeks. Fasting blood is collected before starting the 25% diet (before diet control) and one and seven days before starting GLA and/or PUPA supplementation. Subsequently blood samples are then collected every 7 days after supplementation and 2 weeks after supplementation has ceased.

Analysis of fatty acids and eicosanoids in neutrophils and whole blood.

Fasting (12 h) blood samples are obtained at each of the time points (in all protocols) described above. The following fatty acid and eicosanoid measurements are made at each time point.

Lipid analysis.

Neutrophils and serum are obtained as described above. Lipids are isolated from these blood components and the quantities of fatty acids in these total lipid fractions are determined after base hydrolysis by NICI GC/MS as described. Several fatty acids are analyzed including 20:4 (n-6), 18:2 (n-6), 18:4 (n-3), 20:5 (n-3), 22:6 (n-3), 20:3 (n-9/mead acid), 18:3 (n-3), 18:3 (n-6), 18:1 (n-9), 20:3 (n-6) and 20:4 (n-3). Mead acid has been shown to be an indicator of EFA deficiency. It is possible that the above mentioned diets will change the fatty acid composition of some lipid classes and subclasses while not affecting others. This would give clues as to the potential mechanism of how the diet was influencing eicosanoid generation. However, it is much too labor-intensive and expensive to analyze the fatty acid composition of each lipid class and subclass at each time point of all protocols. Therefore, data is first obtained from fatty acid compositions of total serum and neutrophil lipids. Then PC, PE, PL, PS, triglycerides, free fatty acids and cholesterol esters are isolated by normal phase HPLC from selected samples as described. These samples are selected at time points where differences in total serum or neutrophil lipids are greatest. Phospholipid subclasses are then isolated as diglyceride acetates (see Example 1). Fatty acid compositions in each class and subclass is determined after base hydrolysis by NICI GC/MS as described in the Example 1.

Eicosanoid measurements in whole blood.

Recently, a method to stimulate whole blood with a physiologic (zymosan) or nonphysiologic (A23187) stimulus and measure several 5-lipoxygenase, 12-lipoxygenase and cyclooxygenase products by reverse phase HPLC has been described (Surette et al., 1993a; Surette et al., 1993b). This assay is utilized at each time point to examine whether the diets have selective effects on 5-lipoxygenase or affect other AA metabolizing enzymes such as 12-lipoxygenase or cyclooxygenase. In addition, the assay reveals whether the effects that are observed in isolated neutrophils are mirrored in the whole blood. Briefly, freshly drawn venous blood is obtained from fasted donors at each time point and collected into a 10 ml glass tube containing 140 units of heparin. Cells counts and differentials are obtained in the GCRC. Studies are carried out by stimulating 1 ml aliquots of blood with either unopsonized zymosan or A23187 for 30 min at 37° C. Incubations are terminated by cooling the blood samples in an ice-water bath and plasma obtained by centrifugation. Two hundred microliter aliquots of plasma are denatured with methanol/acetonitrile containing $PGB_2$ as an internal standard. Products including $LTB_4$, $LTC_4$, 20-OH $LTB_4$, 20-carboxy $LTB_4$, 12-HETE and 12 HHT (a cyclooxygenase product) are measured by reverse phase HPLC.

Eicosanoid measurement in neutrophils.

Stimulated neutrophils produce primarily 5-lipoxyoenase products, 5-HETE, $LTB_4$, 20-OH LTB4 and 20-carboxy LTB4. These products along with 15-HETrE, the 15-lipoxygenase product of DGLA, are measured at each time point by HPLC as described in the Example 1.

Measurements of free AA, dihomogammalinolenic acid and eicosapentaenoic acid in stimulated neutrophils.

Stimulated neutrophils release AA from phospholipids utilizing $PLA_2(s)$ reactions. The inventor has also demonstrated that $PLA_2(s)$ recognize DGLA (20:3, n-6) and EPA (20:5, n-3). Therefore, AA, DGLA. EPA are measured by NICI GC/MS before and after stimulation of neutrophils isolated from each volunteer at each dietary time point. Neutrophils are stimulated with ionophore A23187 or LPS or LPS and FMLP as described in Example 1.

Results

The provision of EPA to GLA-supplemented diets will reduce hepatic conversion of DGLA to AA and thus prevent the accumulation of serum AA levels. There is some question as to what effect adding EPA to GLA will have on leukotriene biosynthesis. It is predicted herein that this combination may very well further reduce leukotriene biosynthesis (when compared to GLA alone) since EPA has also been shown to directly compete with AA during AA metabolism.

Example 10

Determination of the Accumulation of ω-3 AA from Stearidonic Acid Treatment of Neutrophils Affects the Capacity of Cells to Release AA and Synthesize Eicosanoids In additional work, the inventor has also demonstrated that human neutrophils rapidly take up stearidonic acid (18:4, n-3) and convert it to ω-3 AA. ω-3 AA is a 20 carbon fatty acid which is a close structural analog of AA (n-6). Thus, the inventor also suggests that ω-3 AA may also serve as a competitive antagonist for AA (n-6) during AA metabolism. The following Examples provide details of procedures used to investigate this strategy.

It is not known whether ω-3 AA-containing phospholipids will influence the capacity of PLA, isotypes to release AA (n-6) in stimulated neutrophils or whether ω-3 AA will affect enzymes distal to phospholipase $A_2$ such as 5-lipoxygenase or cyclooxygenase I and II. These issues are readily explored by 'loading' human neutrophils in vitro with ω-3 AA; then, these cells are then activated and their capacity to release AA, stearidonic acid and ω-3 AA as well as produce eicosanoids is examined. The present Example provides details for carrying out such procedures.

Isolated neutrophils (20 million/40 ml of media) or eosinophils (10 million/40 ml of media) are maintained in culture with RPMI, 2% insulin transferrin, 1% FBS and various concentrations of stearidonic acid (quantities ranging from 0 to 200 nmol). After 24 h, these cells are washed (2x) with flanks Balanced Salt Solution containing 0.25 mg/ml albumin and then resuspended at a concentration of 10 million/ml. Cells then are stimulated with ionophore A23187 (1 μM) and maintained at 37° C. for an additional 5 min. For a more physiologic stimulus, neutrophils are incubated in 10% autologous plasma containing 1 μg/ml LPS for 30 min. Eosinophils are stimulated with PAF (1 μM). Cells are then washed and incubated with or without FMLP (1 μM). Reactions are terminated with methanol/chloroform (2:1, v/v) or methanol for fatty acid release or leukotriene analysis, respectively.

To determine the quantity of fatty acids released from glycerolipids during cell activation, octadeuterated AA and trideuterated stearic acid are added, as internal standards, to the terminated reaction mixture and lipids are extracted by the method of Bligh and Dyer (1959). Fatty acids in samples are then analyzed by NICI GC/MS. Quantities of leukotrienes are determined following reverse phase HPLC separation as described in Example 1. Quantities of prostaglandins are determined by NICI GC/MS. From these studies, it can be determined: 1) Whether the presence of ω-3 AA or stearidonic acid-containing phospholipid in cellular membranes of neutrophils and eosinophils influence the capacity of neutrophil phospholipase $A_2(s)$ to mobilize AA (n-6), 2); Whether ω-3 AA or stearidonic acid is released from membrane glycerolipids during cell activation, and 3) Whether the presence of ω-3 fatty acids effects the capacity of neutrophils and eosinophils to synthesize leukotrienes and prostaglandins.

In addition to examining the effect of ω-3 arachidonic acid on AA metabolism, the inventor also determined whether ω-3 arachidonic acid itself is metabolized by neutrophils to eicosanoid-like products. In these studies, A23187-stimulated and unstimulated neutrophils are incubated with ω-3 arachidonic acid (from 1 to 50 μM for 10 min.). Products are then separated by reverse phase HPLC (see Example 1) and fractions monitored at 234 nM [HETE-like compounds] or 270 [leukotriene-like compounds]. New products observed with ω-3 AA and A23187 addition (not observed with either alone) are isolated and converted to methoxime-pentafluorobenzyl-ester-trimethysilyl ether derivatives as described previously. Derivatized products as carboxylate anions are analyzed by negative ion chemical ionization GC/MS. It is possible that some products of ω-3 AA may not absorb at the above mentioned wavelengths. In this case, there are several HPLC-electrospray mass spectrometry/mass spectrometry procedure for characterizing the double bond positions and position of hydroxyl modifications of fatty acids. These are used to definitively identify products from ω-3 AA.

It is likely that ω-3 AA attenuates the capacity of cells to synthesize leukotrienes. Further, neutrophil $PLA_2(s)$ hydrolyzes ω-3 AA from cellular glycerolipids during cell activation.

Example 11

Effects of in vivo Supplementation with Oils Enriched in Stearidonic Acid (18:4, n-3) on the Quantities and Ratios of n-6 and n-3 Fatty Acid in Serum and Neutrophil Lipids and the Ex Vivo Capacity of Stimulated Neutrophils from Supplemented Volunteers to Release Fatty Acids and Produce Eicosanoids.

The inventor has demonstrated that in vitro incubation (for 24 h) of stearidonic acid with human neutrophils leads to a dramatic increase in the quantity of ω-3 AA in cellular glycerolipids and thus a large increase in the ω-3 AA/AA ratio in these complex lipids. These data indicate that the neutrophil elongase activity can be utilized to synthesize close structural analogs of AA from appropriate dietary precursors. These analogs are then postulated to affect AA metabolism (via phospholipase $A_2$, 5-lipoxygenase or cyclooxygenase I or II.

It is contemplated that there is an in vivo dose-dependent relationship between the quantity of stearidonic acid consumed in diets and the quantities of stearidonic acid, ω-3 AA and eicosapentaenoic acid in serum lipids and ω-3 AA in neutrophil lipids. If ω-3 AA accumulates in neutrophil lipids as predicted and it acts as a competitor with AA (n-6), then it is also likely that increasing stearidonic acid doses will correlate with a further attenuation of leukotriene generation by neutrophils and whole blood and a concomitant increase in ω-3 AA release from cellular phospholipids.

Recruitment of subjects, diet preparations and monitoring diet compliance are all performed as described in Example 1. To limit variability of volunteer's normal diets, four randomly assigned groups of volunteers (10 per group, 5 males and 5 females) are provided identical 25% fat diets for two weeks before starting stearidonic acid (SDA) supplementation. Then one group of volunteers consumes 1.5 g SDA/day; another group consumes 3.0 g SDA/day and a third group consumes 6.0 g SDA/day. A separate (fourth) group of subjects consumes 3.0 g of alpha linoleic acid from Crossential GLA. Crossential GLA is a commercially available oil from Croda which contains >75% of its fatty acids as alpha linolenic acid. This oil contains no stearidonic acid. This control is necessary to test the hypothesis that bypassing the $\Delta^6$ desaturase is necessary to effectively produce analogs of AA ω-3 AA) in inflammatory cells. All groups consume their respective supplement and identical controlled 25% diets for four weeks. Fasting blood is collected before starting the 25% diet (before diet control) and one and seven days before starting the supplementation. Subsequently, fasting blood samples are then collected every 7 days after supplementation and 2 weeks after supplementation has ceased.

Analysis of fatty acids and eicosanoids in neutrophils and whole blood.

Fasting (12 h) blood samples are obtained at each of the time points (in all protocols) described above. The following fatty acid and eicosanoid measurements are made at each time point. Eicosanoid measurements in whole blood and in stimulated neutrophils are performed as described above.

Measurement of free AA, ω-3 AA and stearidonic acid in stimulated neutrophils.

Stimulated neutrophils release AA from phospholipids utilizing $PLA_2$(s) reactions. It is also possible that $PLA_2$(s) recognizes ω-3 AA or SDA-containing phospholipids, or supplementation with SDA blocks the $PLA_2$-induced release of AA in neutrophils. Therefore, free AA, ω-3 AA, SDA and eicosapentaenoic acid are measured by NICI GC/MS before and after stimulation of neutrophils isolated from each volunteer at each dietary time point. Neutrophils are stimulated with ionophore A23187 or LPS or LPS and FMLP. These protocols are described in Example 1.

It is expected that stearidonic acid (like GLA) is both elongated and $\Delta^5$ desaturated in serum compartments to form ω-3 AA and eicosapentaenoic acid (EPA), respectively. It is also contemplated that only ω-3 AA accumulates in neutrophil glycerolipids thus increasing the ω-3 AA/AA ratio. Stearidonic acid containing oils are also expected to induce much higher quantities of ω-3 AA in neutrophil lipids than alpha linolenic acid. It is likely that the accumulation of ω-3 AA translates into a reduction in the capacity of blood cells, the neutrophil in particular, to produce eicosanoids. Again one of the major advantages of stearidonic acid versus GLA as a supplement is that the elongation/$\Delta 5$ desaturase product from this precursor is EPA and not AA. Consequently, even it EPA accumulates in serum components, it will not enhance AA metabolism.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ahmed and Holub, "Alteration and recovery of bleeding times, platelet aggregation and fatty acid composition of individual phospholipids in platelets of human subjects receiving a supplement of cod-liver oil." *Lipids*, 19:617–724, 1984.

American Thoracic Society, "Standards for the diagnosis and care of patients with chronic obstructive pulmonary disease (COPD) and asthma." *Am. Rev. Respir. Dis.*, 136:225–244, 1987.

Antibodies: A Laboratory Manual, Cold Spring Harbor Laboratory, Cold Spring Harbor Press, Cold Spring Harbor, N.Y., 1988.

Arrieta et al., "Synthesis and H-NMR-spectrospopic Investigations of New Curcumin Analoga", *J. Prakt. Chem.*, 334. 656–700. 1991.

Bligh and Dyer, "A rapid method of total lipid extraction and purification," *Can. J. Biochem. Physiol.*, 37:911–920, 1959.

Boudreau et al., "Lack of dose response by dietary n-3 fatty acids at a constant ratio of n-3 to n-6 fatty acids in suppressing eicosanoid biosynthesis from arachidonic acid," *Am. J. Clin. Nutr.*, 54:111–117, 1991.

Calhoun et al., "Characteristics of peripheral blood eosinophils in patients with nocturnal asthma," *Am. Rev. Respir. Dis.*, 145:577–581, 1992.

Chandrasekar et al., "Dietary ω-3 lipids delay the onset and progression of autoimmune pus nephritis by inhibiting transforming growth factor beta mRNA and protein expression,"*J. Autoimmunity*, 8:381–393, 1995.

Chilton-Lopez et al., "Metabolism of gammalinolenic acid in human neutrophils," *J. Immunol.*, 156:2941–2947, 1996.

Chilton et al., "Control of arachidonate levels within inflammatory cells," *Biochem. Biophys. Acta*, 1299:1–15, 1996a.

Chilton et al., "Control of arachidonate levels within inflammatory cells," *Biochim. Biophys. Acta*, 1299:1–15, 1996b.

Chilton et al., "Dietary n-3 fatty acid effects on neutrophil lipid composition and mediator production. Influence on duration and dosage," *J. Clin. Invest.*, 91:115–122, 1993.

Chilton et al., "Metabolism of arachidonic acid," *In. Crystal, West and Barnes*, eds., Lung: Scientific Foundations, Lippincott-Raven Publishers, Chapter 6, 77–88, 1997.

Chilton et al., "Selective acylation of lyso platelet-activating factor by arachidonate in human neutrophils," *J. Biol. Chem.*, 258:7268–7271, 1983.

Christie. "Rapid separation and quantification of lipid classes by high performance liquid chromatography and mass (light-scattering detection)," *J. Lipid Res.*, 26:607–512, 1985.

Clark et al., Philbrick, Holub, "Flaxseed: a potential treatment for lupus nephritis," *Kidney Int.*, 48:475–480, 1995.

Clarke and Jump, "Polyunsaturated fatty acid regulation of hepatic gene transcription," *Lipids*, 31:87-S11, 1996.

Coffey et al., "Membrane association of active 5-lipoxygenase in resting cells. Evidence for novel regulation of the enzyme in the rat alveolar macrophage." *J. Biol. Chem.*, 267:570–576, 1992.

Dahlen et al., "The leukotriene-antagonist ICI-204,219 inhibits the early airway reaction to cumulative bronchial challenge with allergen in atopic asthmatics," *Eur. Respir. J.*, 7:324–331, 1994.

Dang et al., "Effects of dietary fats on fatty acid composition and Δ5 desaturase in normal and diabetic rats," *Lipids*, 24:882–889, 1989.

Dyerberg, and Bang, "Haemostatic function and platelet polyunsaturated fatty acids in Eskimos," *Lancet*, ii:443435, 1979.

Endres et al., "The effect of dietary supplementation with n-3 polyunsaturated fatty acids on the synthesis of interleukin-1 and tumor necrosis factor by mononuclear cells," *N. Engl. J. Med.*, 320:265–271, 1989.

EP 0711 503
EP 0711 503 A2
EP 0713 653
EP 0713 653 A1

Fernandes et al., "Increased TGF-beta and decreased oncogene expression by ω-3 fatty acids in the spleen delays onset of autoimmune disease in B/W mice," *J. Immunol.*, 152:5979–5987, 1994.

Fonteh et al., "Evidence that secretory phospholipase A2 plays a role in arachidonic acid release and eicosanoid biosynthesis by mast cells," *J. Immunol.*, 162:5438–5446, 1994.

Fonteh et al., "Regulation of arachidonic acid, eicosanoid, and phospholipase $A_2$ levels in murine mast cells by recombinant stem cell factor," *J. Clin. Invest.*, 96: 1432–1439, 1995.

Freifelder, *Physical Biochemistry Applications to Biochemistry and Molecular Biology*, 2nd ed. Wm. Freeman and Co., New York, N.Y., 1982.

Friedman et al, "Decreased prostaglandin E turnover in infants with essential fatty acid deficiency," *Pediati. Res.*, 12:711–714, 1978.

Fukuda et al., "Increased numbers of hypodense eosinophils in the blood of patients with bronchial asthma," *Am. Rev. Respir. Dis.*, 132:981–985, 1985.

Galloway et al., "Effects of dietary fish oil supplementation on the fatty acid composition of the human platelet membrane: demonstration of selectivity in the incorporation of eicosapentaenoic acid into membrane phospholipids," *Clin. Sci.*, 68:449454, 1985.

Gronn et al., "Dietary n-6 fatty acids inhibit the incorporation of dietary n-3 fatty acids in thrombocyte and serum phospholipids in humans: a controlled dietetic study," *Stand. J. Clin. Lab. Invest.*, 51:255–263, 1991.

Gronn et al., "Effects of dietary purified eicosapentaenoic acid and docosahexaenoic acid on fatty acid desaturation and oxidation in isolated rat liver cells," *Biochim. Biophys. Acta*, 1125:3543, 1992.

Hodges et al., "Heterogeneity of leukotriene $C_4$ production by eosinophils from asthmatic and from normal subjects." *Am. Rely. Respir. Dis.*, 138:799–804, 1988.

Horrobin, "Nutritional and medical importance of gamma-linolenic acid," *J. Lipid Res.*, 31:163–194, 1992.

Hurd et al., "Prevention of glomerulonephritis and prolonged survival in New Zealand black/New Zealand white $F_1$ hybrid mice fed an essential fatty acid-deficient diet," *J. Clin. Invest.*, 67:476–482, 1981.

Johnson et al., "Dietary supplementation with γ-linolenic acid alters fatty acid content and eicosanoid production in healthy humans. *J. Nutr.*, 127:1435–1444, 1997.

Kelley et al., "A fish oil diet rich in eicosapentaenoic acid reduces cyclooxygenase metabolites, and suppresses lupus in mRL-1 pr mice," *J. Immunol.*, 134:1914–1919, 1985.

Kerins et al., "Prostacyclin and prostaglandin $E_1$: molecular mechanisms and therapeutic utility," *Prog. Hemostasis Thromb.*, 10:307–337, 1991.

Kikawa et al., "Urinary leukotriene $E_4$ after exercise challenge in children with asthma," *J. Allergy Clin. Immunol.*, 89:1111–1119, 1992.

Kojima et al., "Long-term administration of highly purified eicosapentaenoic acid provides improvement of psoriasis," *Dermatologica*, 182:225–230, 1991.

Lands et al., "Maintenance of lower proportions of (n-6) eicosanoid precursors in phospholipids of human plasma in response to added dietary (n-3) fatty acids," *Biochim. Biophys. Acta*, 1180: 147–162, 1992.

Larsson-Backstrom et al., "Effects of dietary alpha- and gamma-linolenic acids on liver fatty acids, lipid metabolism, and survival in sepsis," *Shock*, 4:11–20, 1995.

Letkowith et al., "Manipulation of the acute inflammatory response by dietary polyunsaturated fatty acid modulation," *J. Immunol.*, 145:1523–1529, 1990.

Leventhal et al., "Treatment of rheumatoid arthritis with gammalinolenic acid," *Ann. Intern. Med.*, 119:867–873, 1993.

Liu et. al., "Evidence for elevated levels of histamine, prostaglandin $D_2$, and other bronchoconstricting prostaglandins in the airways of subjects with mild asthma," *Am. Rev. Respir. Dis.*, 142: 126–132, 1990.

Lykens et al., "Antioxidant activity of bronchoalveolar lavage fluid in the adult respiratory distress syndrome," *Am. J. Physiol. Lung Cell Mol. Physiol.*, 262L:169–L1175, 1992.

Manning et al., "Urinary leukotriene $F_4$ levels during early and late asthmatic response," *J. Allergy Clin. Immun.*, 86:211–220, 1990.

Mead et al., Lipid: Chemistry, Biochemistry and Nutrition, Plenum Press, New York. 1986.

Mehta et al., "Increased leukocyte phospholipase $A_2$ activity and plasma lysophosphatidylcholine levels in asthma and rhinitis and their relationship to airway sensitivity to histamine, *Am. Rev. Respir. Dis.*, 142:157–161, 1990.

Melchert et al., "Fatty acid patterns in triglycerides, diglycerides, fatty acids, cholesterol esters, and phosphatidylcholine from vegetarians and nonvegetarians," *Atheroscler.*, 65:159–166, 1987.

Miller et al., "Dietary supplementation with oils rich in (n-3) and (n-6) fatty acids influences in vivo levels of epidermal lipoxygenase products in guinea pigs," *J. Nutr.*, 120:36–44, 1990.

Mori et al., "New findings in the fatty acid composition of individual platelet phospholipids in man after dietary fish oil supplementation," *Lipids*, 22:744–750, 1987.

Nathan et al., "Inhaled ICI 204,219 blocks antigen-induced bronchoconstriction in subjects with bronchial asthma," *Chest*, 105:483488, 1994.

Nordstrom et al., "Alpha-linolenic acid in the treatment of rheumatoid arthritis. A double-blind, placebo-controlled and randomized study: flaxseed vs. safflower seed," *Rheumatol Int.*, 14;231–234, 1995.

O'Sullivan et al., "Lipopolysaccharide priming of alveolar macrophages for enhanced synthesis of prostanoids involves induction of a novel prostaglandin H synthase," *J. Biol. Chem.*, 267:14547–14550, 1992.

Payan et al., "Alterations in human leukocyte function induced by ingestion of eicosapentaenoic acid," J. Clin. Immunol., 6:402–410 1986.

Pedersen et al., "Synthesis of Naturally Occurring Curcuminoids and Related Compounds", *Ann. Chem.*, 1557–69, 1985.

Phinney et al., "Reduced arachidonate in serum phospholipids and cholesteryl esters associated with vegetarian diets in human," *Am. J. Clin. Nutr.*, 51 :385–392, 1990.

Prickett et al., "Dietary enrichment with the polyunsaturated eicosapentaenoic acid prevents proteinuria and prolongs survival in NZB×NZWF$_1$ mice," *J. Clin. Invest.*, 68:556–559, 1981.

*Remington's Pharmaceutical Sciences*, 15th ed., pp. 1035–1038 and 1570–1580.

Roberge et al., "In vitro leukotriene (LT) C$_4$ synthesis by blood eosinophils from atopic asthmatics: Predominance of eosinophil subpopulations with high potency for LTB$_4$ generation," Prostaglandins Leukotr. Essen Fatty Acids, 41:243–249, 1990.

Rosenthal and Hills, "Elongation of arachidonic and eicosapentaenoic acids limits their availability for thrombin-stimulated release from the glycerolipids of vascular endothelial cells," *Biochim. Biophys. Acta*, 875:382–391, 1986.

Roughly et al., "Experiments in the Biosynthesis of Curcumin", *JCS Perkins Trans I, I*, 2379–88. 1973.

Rovin et al., "Mechanisms underlying the anti-inflammatory effects of essential fatty acid deficiency in experimental glomerulonephritis. Inhibited release of a monocyte chemoattractant by glomeruli," J. Immunol., 145:1238–1245, 1990.

Samet et al., "Selective induction of prostaglandin G/H synthase I by stem cell factor and dexamethasone in mast cells," *J. Biol. Chem.*, 270:8044–8049, 1995.

Samuelsson et al., "Leukotrienes and lipoxins: structures, biosynthesis, and biological effects," *Science*, 237:1171–1176, 1987.

Sanders et al., "Studies of vegans: the fatty acid composition of plasma choline phosphoglycerides, erythrocytes, adipose tissue, and breast milk, and some indicators of susceptibility to ischemic heart disease in vegans and omnivore controls." *Am. J. Clin. Nutr.*, 31:805–813, 1978.

Seyberth et al., "Increased arachidonate in lipids alter administration to man: Effects on prostaglandin biosynthesis," *Clin. Pharmacol. Ther.*, 18:521–529, 1975.

Shin et al. "Nasal allergen challenge generates 1-O-hexadecyl-2-lyso-sn-glycero-3-phosphocholine," *Am. J. Respir. Crit. Care Med.*, 149:660–666. 1994.

Shoda et al., "Therapeutic efficacy of N-3 polyunsaturated fatty acid in experimental Crohn's disease," *J. Gistroenterol*, 30suppl 8):98–101, 1995.

Smith et al., "Inhibition of leukotriene D4-induced bronchoconstriction in subjects with asthma: a concentration-effect study of ICI 204,219," Clin. Pharm. Ther., 54:430–4366, 1993.

Smith et al., "Inflammatory cells and eicosanoid mediators in subjects with late asthmatic responses and increases in airway responsiveness," *J. Allergy Clin. Immunol.*, 89:1076–1084, 1992.

Sperling et al., "The effects on n-3 polyunsaturated fatty acids on the generation of platelet activating factor-acether by human monocytes," *J. Immunol.*, 139:41864191, 1987.

Stadel et al., "Characterization of phospholipase A$_2$ from human nasal lavage," *Am. J. Respir. Cell. Mol. Biol.*, 11:108–113, 1994.

Strasser et al., "Leukotriene B$_5$ is formed in human neutrophils after dietary supplementation with eicosapentaenoic acid," *Proc. Natl. Acad. Sci. USA*, 82:1540–1543, 1984.

Surette et al., "Lipopolysaccharides prime whole human blood and isolated neutrophils for the increased synthesis of 5-lipoxygenase products by enhancing arachidonic acid availability: involvement of the CD14 antigen," *J. Exp. Med.*, 178:1347–1355, 1993b.

Surette et al., "Reverse phase HPLC analysis of arachidonate metabolites in whole blood stimulated ex vivo," *Anal. Biochem.* 216:392–400, 1993a.

Tate et al., "Suppression of acute and chronic intimation by dietary gamma linolenic acid, *J. Rheum.*, 16:729–734, 1989.

Triggiani et al., "Evidence that increasing the cellular content of eicosapentaenoic acid does not reduce the biosynthesis of platelet-activating factor, *J. Immunol.*, 145:2241–2248, 1990.

Triggiani et al., *J. Exp. Med.*, 1892:1181, 1985.

U.S. Pat. No. 4,196,265
U.S. Pat. No. 4,309,415
U.S. Pat. No. 4,367,110
U.S. Pat. No. 4,386,072
U.S. Pat. No. 4,444,755
U.S. Pat. No. 4,452,901
U.S. Pat. No. 4,576,758
U.S. Pat. No. 4,666,701
U.S. Pat. No. 4,888,326
U.S. Pat. No. 4,965,075
U.S. Pat. No. 5,178,873
U.S. Pat. No. 5,209,826
U.S. Pat. No. 5,215,630
U.S. Pat. No. 5,221,605
U.S. Pat. No. 5,238,808
U.S. Pat. No. 5,246,841
U.S. Pat. No. 5,246,842
U.S. Pat. No. 5,310,687
U.S. Pat. No. 5,328,691
U.S. Pat. No. 5,336,496
U.S. Pat. No. 5,352,700
U.S. Pat. No. 5,401,646
U.S. Pat. No. 5,567,732
U.S. Pat. No. 5,674,853
U.S. Pat. No. 5,679,864
U.S. Pat. No. 5,683,898

USDA Handbook 8 and The Nutrition Data System from The Nutritional Coordinating Center Vanderhoek et al., "Inhibition of leukotriene biosynthesis by the leukocyte product 15-hydroxy-5,8, 11, 13-eicosatetraenoic acid," *J. Biol. Chem.*, 255:10064–10066, 1980.

Wardlaw et al., "Leukotrienes, LTC$_4$ and LTB$_4$, in bronchoalveolar lavage in bronchial asthma and other respiratory diseases," *J. Allergy Clin. Immunol.*, 84: 19–26, 1989.

Welch et al., "Effect of RG 12525, a new leukotriene antagonist, on pulmonary function of asthmatic adults," *Ann. Allergy*, 72:348–352, 1994.

Wene et al., "The development of essential fatty acid deficiency in healthy men fed fat-free diets intravenously and orally," *J. Clin. Invest.*, 56:127–34, 1975.

Wensing et al., "effect of BAY×7195, an oral receptor antagonist of cysteinyl-leukotrienes, on leukotriene D4-induced bronchoconstriction in normal volunteers," *Eur. J. Clin. Pharm.*, 47:227–230, 1994.

Wenzel et al., "Bronchoalveolar lavage fluid mediator levels 5 minutes after allergen challenge in atopic subjects with asthma: relationship to the development of late asthmatic responses," *J. Allergy Clin. Immunol*, 87:540–548, 1991.

Wenzel et al., "Bronchoscopic evaluation of severe asthma. Persistent inflammation associated with high dose glucocorticoids," *Am. J. Respir. Crit. Care Med.*, 156:737–743, 1997.

Wenzel et al., "Spectrum of prostanoid release after bronchoalveolar allergen challenge in atopic asthmatics and in control groups: An alteration in the ratio of bronchoconstrictive to bronchoprotective mediators," *Am. Rev. Respir. Dis.*, 139:450–458, 1989.

Westcott et al., "Urinary leukotriene $E_4$ in patients with asthma," *Am. Rev. Respir. Dis.*, 143: 1322–1328, 1991.

WO 96/31457

WO 97/21434

Zehr et al, "Use of segmental airway lavage to obtain relevant mediators from the lungs of asthmatic and control subjects," *Chest*, 95:1059–1063, 1989.

Zibok and Fletcher, "Dose-response effects of dietary gamma-linolenic acid-enriched oils on human polymorphonuclear-neutrophil biosynthesis of leukotriene $B_4$, *Am. J. Clin. Nutr.*, 55:39–45, 1992.

What is claimed is:

1. A method of inhibiting an increase in serum arachidonic acid of a mammal to which γ-linolenic acid (GLA) is provided, comprising providing to said mammal a $\Delta^5$ desaturase inhibitor.

2. The method of claim 1, wherein said $\Delta^5$ desaturase inhibitor is eicosapentaenoic acid (EPA), sesamin, curcumin, heneicosapentaenoic acid, or docosahexaenoic acid.

3. The method of claim 2, wherein said GLA and EPA are administered as free fatty acids.

4. The method of claim 2, wherein said said GLA and EPA are administered as fatty acyl esters.

5. The method of claim 4, wherein said esters are selected from the group consisting of triglycerides, ethyl esters, phospholipids, steryl esters, and sphingolipids.

6. The method of claim 1, wherein said mammal has an inflammatory disorder.

7. The method of claim 2, wherein said GLA and said EPA are administered in a single composition.

8. The method of claim 2, wherein said GLA and said EPA are administered in distinct compositions.

9. A method of treating an inflammatory disorder in a mammal comprising providing to said mammal:

(a) γ-linolenic acid in an amount effective to increase the amount of dihomogammalinolenic acid (DGLA) in the inflammatory cells of said mammal; and (b) $\Delta^5$ desaturase inhibitor in an amount effective to inhibit an increase in arachidonic acid in the serum of said mammal;

wherein the increase in DGLA in the inflammatory cells of said mammal decreases the inflammatory response in said mammal;

and further wherein said treating does not include providing a salt of magnesium, manganese, chondroitin, n-acetyl glucosamine or glucosamine.

10. The method of claim 9, wherein said $\Delta^5$ desaturase inhibitor is EPA.

11. The method of claim 9, wherein said inflammatory disease is asthma, allergic rhinitis, allergic rhinoconjunctivitis, arthritis, psoriasis, acute myocardial infarction, glomerulonephritis, Crohn's disease, or inflammatory bowel disease.

* * * * *